(12) United States Patent
Marsot et al.

(10) Patent No.: US 10,820,954 B2
(45) Date of Patent: Nov. 3, 2020

(54) ALIGNMENT AND ATTACHMENT SYSTEMS FOR MEDICAL INSTRUMENTS

(71) Applicant: Auris Health, Inc., Redwood City, CA (US)

(72) Inventors: Travis R. Marsot, Mountain View, CA (US); Aren Calder Hill, Mountain View, CA (US); Travis Michael Schuh, Los Altos, CA (US); Spencer James Witte, San Francisco, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/357,763

(22) Filed: Mar. 19, 2019

(65) Prior Publication Data

US 2020/0000537 A1     Jan. 2, 2020

Related U.S. Application Data

(60) Provisional application No. 62/690,744, filed on Jun. 27, 2018.

(51) Int. Cl.
*A61B 34/00*         (2016.01)
*A61B 34/37*         (2016.01)
(Continued)

(52) U.S. Cl.
CPC ............ *A61B 34/70* (2016.02); *A61B 1/0016* (2013.01); *A61B 34/37* (2016.02); *A61B 90/50* (2016.02);
(Continued)

(58) Field of Classification Search
CPC ......... A61B 34/70; A61B 34/37; A61B 90/50; A61B 1/0016
See application file for complete search history.

(56) References Cited

U.S. PATENT DOCUMENTS

| 2,556,601 A | 6/1951 | Schofield |
| 2,566,183 A | 8/1951 | Forss |

(Continued)

FOREIGN PATENT DOCUMENTS

| CN | 103037799 | 4/2011 |
| CN | 102665590 | 9/2012 |

(Continued)

OTHER PUBLICATIONS

Mayo Clinic, Robotic Surgery, https://www.mayoclinic.org/tests-procedures/robotic-surgery/about/pac-20394974?p=1, downloaded from the internet on Jul. 12, 2018, 2 pp.

(Continued)

*Primary Examiner* — Julie A Szpira
(74) *Attorney, Agent, or Firm* — Knobbe Martens Olsen & Bear LLP

(57) ABSTRACT

A medical instrument can include alignment and attachment mechanisms for aligning and attaching the medical instrument to another device, such as an adapter on an instrument drive mechanism. For example, a medical system can include a medical instrument having an instrument handle and an elongated body. The system can include an alignment mechanism configured to provide rotational alignment between the medical instrument and an adapter. The system can also include an attachment mechanism configured to secure the medical instrument to the adapter. The attachment mechanism can include at least three locking elements positioned circumferentially about the axis.

19 Claims, 23 Drawing Sheets

(51) Int. Cl.
*A61B 90/50* (2016.01)
*A61B 1/00* (2006.01)
*B25J 9/00* (2006.01)
*B25J 15/00* (2006.01)
*B25J 13/06* (2006.01)
*A61B 34/30* (2016.01)

(52) U.S. Cl.
CPC ......... *B25J 9/0084* (2013.01); *B25J 15/0019* (2013.01); *A61B 2034/301* (2016.02); *A61B 2034/303* (2016.02); *A61B 2034/305* (2016.02); *B25J 13/06* (2013.01)

(56) References Cited

U.S. PATENT DOCUMENTS

| | | | |
|---|---|---|---|
| 2,623,175 A | 12/1952 | Finke | |
| 2,730,699 A | 1/1956 | Gratian | |
| 2,884,808 A | 5/1959 | Mueller | |
| 3,294,183 A | 12/1966 | Riley et al. | |
| 3,472,083 A | 10/1969 | Schnepel | |
| 3,513,724 A | 5/1970 | Box | |
| 3,595,074 A | 7/1971 | Johnson | |
| 3,734,207 A | 5/1973 | Fishbein | |
| 3,739,923 A | 6/1973 | Totsuka | |
| 3,784,031 A | 1/1974 | Nitu | |
| 3,921,536 A | 11/1975 | Savage | |
| 3,926,386 A | 12/1975 | Stahmann | |
| 4,141,245 A | 2/1979 | Brandstetter | |
| 4,241,884 A | 12/1980 | Lynch | |
| 4,243,034 A | 1/1981 | Brandt | |
| 4,351,493 A | 9/1982 | Sonnek | |
| 4,357,843 A | 11/1982 | Peck et al. | |
| 4,384,493 A | 5/1983 | Grunbaum | |
| 4,507,026 A | 3/1985 | Lund | |
| 4,530,471 A | 7/1985 | Inoue | |
| 4,555,960 A | 12/1985 | King | |
| 4,688,555 A | 8/1987 | Wardle | |
| 4,745,908 A | 5/1988 | Wardle | |
| 4,784,150 A | 11/1988 | Voorhies et al. | |
| 4,857,058 A | 8/1989 | Payton | |
| 4,907,168 A | 3/1990 | Boggs | |
| 4,945,790 A | 8/1990 | Golden | |
| 5,207,128 A | 5/1993 | Albright | |
| 5,234,428 A | 8/1993 | Kaufman | |
| 5,256,150 A | 10/1993 | Quiachon et al. | |
| 5,277,085 A | 1/1994 | Tanimura et al. | |
| 5,350,101 A | 9/1994 | Godlewski | |
| 5,426,687 A | 6/1995 | Goodall et al. | |
| 5,507,725 A | 4/1996 | Savage et al. | |
| 5,524,180 A | 6/1996 | Wang et al. | |
| 5,559,294 A | 9/1996 | Hoium et al. | |
| 5,709,661 A | 1/1998 | Van Egmond | |
| 5,767,840 A | 6/1998 | Selker | |
| 5,779,623 A | 7/1998 | Bonnell | |
| 5,792,135 A | 8/1998 | Madhani et al. | |
| 5,855,583 A | 1/1999 | Wang et al. | |
| 5,921,968 A | 7/1999 | Lampropoulos et al. | |
| 5,967,934 A | 10/1999 | Ishida et al. | |
| 6,077,219 A | 6/2000 | Viebach | |
| 6,084,371 A | 7/2000 | Kress et al. | |
| 6,154,000 A | 11/2000 | Rastegar et al. | |
| 6,171,234 B1 | 1/2001 | White et al. | |
| 6,185,478 B1 | 2/2001 | Koakutsu et al. | |
| 6,272,371 B1 | 8/2001 | Shlomo | |
| 6,289,579 B1 | 9/2001 | Viza et al. | |
| 6,394,998 B1 | 5/2002 | Wallace et al. | |
| 6,401,572 B1 | 6/2002 | Provost | |
| 6,413,264 B1* | 7/2002 | Jensen et al. | |
| 6,436,107 B1 | 8/2002 | Wang et al. | |
| 6,451,027 B1* | 9/2002 | Cooper et al. | |
| 6,487,940 B2 | 12/2002 | Hart et al. | |
| 6,491,701 B2 | 12/2002 | Tierney et al. | |
| 6,695,818 B2 | 2/2004 | Wollschlager | |
| 6,726,675 B1 | 4/2004 | Beyar | |
| 6,786,896 B1 | 9/2004 | Madhani et al. |
| 6,827,712 B2 | 12/2004 | Tovey et al. |
| 7,044,936 B2 | 5/2006 | Harding |
| 7,172,580 B2 | 2/2007 | Hruska et al. |
| 7,276,044 B2 | 10/2007 | Ferry et al. |
| 7,615,042 B2 | 11/2009 | Beyar et al. |
| 7,635,342 B2 | 12/2009 | Ferry et al. |
| 7,766,856 B2 | 8/2010 | Ferry et al. |
| 7,938,809 B2 | 5/2011 | Lampropoulos et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,157,308 B2 | 4/2012 | Pedersen |
| 8,182,415 B2 | 5/2012 | Larkin et al. |
| 8,277,417 B2 | 10/2012 | Fedinec et al. |
| 8,291,791 B2 | 10/2012 | Light et al. |
| 8,414,505 B1 | 4/2013 | Weitzner |
| 8,425,465 B2 | 4/2013 | Nagano |
| 8,671,817 B1 | 3/2014 | Bogusky |
| 8,720,448 B2 | 5/2014 | Reis et al. |
| 8,746,252 B2 | 6/2014 | McGrogan et al. |
| 8,870,815 B2 | 10/2014 | Bhat et al. |
| 8,961,533 B2 | 2/2015 | Stahler et al. |
| 8,968,333 B2 | 3/2015 | Yu et al. |
| 8,992,542 B2 | 3/2015 | Hagag et al. |
| 9,173,713 B2 | 11/2015 | Hart et al. |
| 9,204,933 B2 | 12/2015 | Reis et al. |
| 9,326,822 B2 | 5/2016 | Lewis et al. |
| 9,408,669 B2 | 8/2016 | Kokish et al. |
| 9,446,177 B2 | 9/2016 | Millman et al. |
| 9,452,018 B2 | 9/2016 | Yu |
| 9,457,168 B2 | 10/2016 | Moll et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,136,959 B2 | 11/2018 | Mintz et al. |
| 10,143,360 B2 | 12/2018 | Roelle et al. |
| 10,145,747 B1 | 12/2018 | Lin et al. |
| 10,149,720 B2 | 12/2018 | Romo |
| 10,159,532 B1 | 12/2018 | Ummalaneni |
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,874 B2 | 3/2019 | Yu et al. |
| 10,231,793 B2 | 3/2019 | Romo |
| 10,231,867 B2 | 3/2019 | Alvarez et al. |
| 10,405,939 B2 | 9/2019 | Romo et al. |
| 10,405,940 B2 | 9/2019 | Romo |
| 10,426,661 B2 | 10/2019 | Kintz |
| 10,434,660 B2 | 10/2019 | Meyer |
| 10,464,209 B2 | 11/2019 | Ho et al. |
| 10,470,830 B2 | 11/2019 | Hill |
| 10,482,599 B2 | 11/2019 | Mintz et al. |
| 10,517,692 B2 | 12/2019 | Eyre et al. |
| 10,524,866 B2 | 1/2020 | Srinivasan |

(56) References Cited

U.S. PATENT DOCUMENTS

| | | |
|---|---|---|
| 10,539,478 B2 | 1/2020 | Lin |
| 10,555,778 B2 | 2/2020 | Ummalaneni et al. |
| 2001/0042643 A1 | 11/2001 | Krueger et al. |
| 2002/0045905 A1 | 4/2002 | Gerbi et al. |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0111635 A1* | 8/2002 | Jensen et al. |
| 2002/0117017 A1 | 8/2002 | Bernhardt et al. |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0056561 A1 | 3/2003 | Butscher et al. |
| 2003/0212308 A1 | 11/2003 | Bendall |
| 2004/0015053 A1 | 1/2004 | Bieger |
| 2004/0152972 A1 | 8/2004 | Hunter |
| 2004/0243147 A1 | 12/2004 | Lipow |
| 2004/0254566 A1 | 12/2004 | Plicchi |
| 2005/0004579 A1 | 1/2005 | Schneider et al. |
| 2005/0177026 A1 | 8/2005 | Hoeg et al. |
| 2005/0183532 A1 | 8/2005 | Najafi et al. |
| 2005/0222554 A1 | 10/2005 | Wallace et al. |
| 2006/0041245 A1 | 2/2006 | Ferry |
| 2006/0111692 A1 | 5/2006 | Hlavka et al. |
| 2006/0146010 A1 | 7/2006 | Schneider |
| 2006/0201688 A1 | 9/2006 | Jenner et al. |
| 2006/0229587 A1 | 10/2006 | Beyar et al. |
| 2006/0237205 A1 | 10/2006 | Sia et al. |
| 2007/0000498 A1 | 1/2007 | Glynn et al. |
| 2007/0013336 A1 | 1/2007 | Nowlin et al. |
| 2007/0060879 A1 | 3/2007 | Weitzner et al. |
| 2007/0100201 A1* | 5/2007 | Komiya et al. |
| 2007/0100254 A1 | 5/2007 | Murakami |
| 2007/0112355 A1 | 5/2007 | Salahieh |
| 2007/0119274 A1 | 5/2007 | Devengenzo et al. |
| 2007/0149946 A1 | 6/2007 | Viswanathan |
| 2007/0191177 A1 | 8/2007 | Nagai et al. |
| 2007/0239028 A1 | 10/2007 | Houser |
| 2007/0245175 A1 | 10/2007 | Zheng et al. |
| 2007/0299427 A1* | 12/2007 | Yeung et al. |
| 2008/0039255 A1 | 2/2008 | Jinno et al. |
| 2008/0046122 A1* | 2/2008 | Manzo et al. |
| 2008/0065103 A1 | 3/2008 | Cooper et al. |
| 2008/0147011 A1 | 6/2008 | Urmey |
| 2008/0177285 A1 | 7/2008 | Brock et al. |
| 2008/0214925 A1 | 9/2008 | Wilson et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0287963 A1 | 11/2008 | Rogers et al. |
| 2008/0302200 A1 | 12/2008 | Tobey |
| 2009/0000626 A1* | 1/2009 | Quaid et al. |
| 2009/0082722 A1 | 3/2009 | Munger et al. |
| 2009/0098971 A1 | 4/2009 | Ho et al. |
| 2009/0105645 A1 | 4/2009 | Kidd et al. |
| 2009/0112060 A1* | 4/2009 | Sugiyama et al. |
| 2009/0163948 A1 | 6/2009 | Sunaoshi |
| 2009/0171371 A1 | 7/2009 | Nixon |
| 2009/0247944 A1 | 10/2009 | Kirschenman et al. |
| 2009/0248039 A1 | 10/2009 | Cooper et al. |
| 2009/0292298 A1* | 11/2009 | Lin et al. |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0130923 A1 | 5/2010 | Cleary et al. |
| 2010/0130987 A1 | 5/2010 | Wenderow et al. |
| 2010/0175701 A1 | 7/2010 | Reis et al. |
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2010/0249506 A1 | 9/2010 | Prisco et al. |
| 2010/0274078 A1 | 10/2010 | Kim et al. |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028991 A1 | 2/2011 | Ikeda et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0238083 A1* | 9/2011 | Moll et al. |
| 2011/0261183 A1 | 10/2011 | Ma et al. |
| 2011/0277775 A1* | 11/2011 | Holop et al. |
| 2011/0288573 A1 | 11/2011 | Yates et al. |
| 2011/0306836 A1 | 12/2011 | Ohline et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0118088 A1* | 5/2012 | Smith et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0232476 A1 | 9/2012 | Bhat et al. |
| 2012/0239012 A1 | 9/2012 | Laurent et al. |
| 2012/0277730 A1 | 11/2012 | Salahieh |
| 2012/0283747 A1 | 11/2012 | Popovic |
| 2012/0289973 A1* | 11/2012 | Prisco et al. |
| 2013/0018400 A1 | 1/2013 | Milton et al. |
| 2013/0144116 A1 | 6/2013 | Cooper et al. |
| 2013/0231678 A1 | 9/2013 | Wenderow |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1* | 1/2014 | Shelton, IV et al. |
| 2014/0066944 A1 | 3/2014 | Taylor et al. |
| 2014/0069437 A1 | 3/2014 | Reis et al. |
| 2014/0142591 A1 | 5/2014 | Alvarez et al. |
| 2014/0151430 A1* | 6/2014 | Scheib et al. |
| 2014/0166023 A1 | 6/2014 | Kishi |
| 2014/0171778 A1 | 6/2014 | Tsusaka |
| 2014/0222019 A1 | 8/2014 | Brudnick |
| 2014/0243849 A1 | 8/2014 | Saglam et al. |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276935 A1 | 9/2014 | Yu |
| 2014/0276936 A1 | 9/2014 | Kokish et al. |
| 2014/0277334 A1* | 9/2014 | Yu et al. |
| 2014/0357984 A1 | 12/2014 | Wallace et al. |
| 2014/0364870 A1 | 12/2014 | Alvarez et al. |
| 2015/0012134 A1 | 1/2015 | Robinson |
| 2015/0038981 A1* | 2/2015 | Kilroy et al. |
| 2015/0051592 A1 | 2/2015 | Kintz |
| 2015/0090063 A1 | 4/2015 | Lantermann et al. |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0164594 A1 | 6/2015 | Romo et al. |
| 2015/0164596 A1 | 6/2015 | Romo |
| 2015/0182250 A1 | 7/2015 | Conlon et al. |
| 2015/0231364 A1 | 8/2015 | Blanchard |
| 2015/0327939 A1 | 11/2015 | Kokish et al. |
| 2015/0335480 A1 | 11/2015 | Alvarez et al. |
| 2015/0374445 A1 | 12/2015 | Gombert et al. |
| 2016/0000512 A1 | 1/2016 | Gombert et al. |
| 2016/0001038 A1 | 1/2016 | Romo et al. |
| 2016/0157945 A1 | 6/2016 | Madhani |
| 2016/0166234 A1 | 6/2016 | Zhang |
| 2016/0184037 A1* | 6/2016 | Cooper et al. |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0374541 A1 | 12/2016 | Agrawal et al. |
| 2017/0007337 A1 | 1/2017 | Dan |
| 2017/0007343 A1 | 1/2017 | Yu |
| 2017/0071684 A1 | 3/2017 | Kokish et al. |
| 2017/0100199 A1 | 4/2017 | Yu et al. |

(56) References Cited

U.S. PATENT DOCUMENTS

| | | |
|---|---|---|
| 2017/0105804 A1 | 4/2017 | Yu |
| 2017/0119481 A1 | 5/2017 | Romo et al. |
| 2017/0151028 A1 | 6/2017 | Ogawa et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209672 A1 | 7/2017 | Hart et al. |
| 2017/0252540 A1 | 9/2017 | Weitzner et al. |
| 2017/0281049 A1 | 10/2017 | Yamamoto |
| 2017/0290631 A1 | 10/2017 | Lee et al. |
| 2017/0296784 A1 | 10/2017 | Kokish |
| 2017/0312481 A1 | 11/2017 | Covington et al. |
| 2017/0333679 A1 | 11/2017 | Jiang |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0049792 A1 | 2/2018 | Eckert |
| 2018/0056044 A1 | 3/2018 | Choi et al. |
| 2018/0104820 A1 | 4/2018 | Troy et al. |
| 2018/0116735 A1 | 5/2018 | Tierney et al. |
| 2018/0177383 A1 | 6/2018 | Noonan et al. |
| 2018/0177556 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0296299 A1 | 10/2018 | Iceman |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0110839 A1 | 4/2019 | Rafii-Tari et al. |
| 2019/0151148 A1 | 4/2019 | Alvarez et al. |
| 2019/0142537 A1 | 5/2019 | Covington et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0086087 A1 | 3/2020 | Hart et al. |
| 2020/0091799 A1 | 3/2020 | Covington et al. |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0101264 A1 | 4/2020 | Jiang |

FOREIGN PATENT DOCUMENTS

| | | |
|---|---|---|
| CN | 102015759 | 4/2013 |
| DE | 19649082 | 1/1998 |
| DE | 102004020465 | 9/2005 |
| EP | 1 442 720 | 8/2004 |
| EP | 2 567 670 | 3/2013 |
| EP | 3 025 630 | 6/2016 |
| JP | 07-136173 | 5/1995 |
| JP | 2009-139187 | 6/2009 |
| JP | 2010-046384 | 3/2010 |
| WO | WO 02/74178 | 9/2002 |
| WO | WO 07/146987 | 12/2007 |
| WO | WO 09/092059 | 7/2009 |
| WO | WO 11/005335 | 1/2011 |
| WO | WO 12/037506 | 3/2012 |
| WO | WO 13/179600 | 12/2013 |
| WO | WO 15/127231 | 8/2015 |
| WO | WO 17/059412 | 4/2017 |
| WO | WO 17/0151993 | 9/2017 |

OTHER PUBLICATIONS

International search report and written opinion dated Jul. 22, 2019 for PCT/US2019/23016.

\* cited by examiner

ALIGNMENT AND ATTACHMENT SYSTEMS FOR MEDICAL INSTRUMENTS

INCORPORATION BY REFERENCE TO ANY PRIORITY APPLICATIONS

This application claims priority to U.S. Provisional Application No. 62/690,744, filed Jun. 27, 2018, which is incorporated herein by reference. Any and all applications for which a foreign or domestic priority claim is identified in the Application Data Sheet as filed with the present application are hereby incorporated by reference under 37 CFR 1.57.

TECHNICAL FIELD

This application relates to alignment and attachment systems and methods for medical instruments. In some embodiments, the alignment and attachment systems and methods can be used with robotic medical systems and instruments.

BACKGROUND

Medical procedures, such as laparoscopy, may involve accessing and visualizing an internal region of a patient. In a laparoscopic procedure, a medical instrument can be inserted into the internal region through a laparoscopic access port.

In certain procedures, a robotically-enabled medical system may be used to control the insertion and/or manipulation of the medical instrument. The robotically-enabled medical system may include a robotic arm, or other instrument positioning device, to which the medical instrument can be attached.

SUMMARY

Alignment and attachment systems for medical instruments are described herein. In some embodiments, the alignment systems are configured to align a medical instrument with a corresponding adapter, and the attachment systems are configured to attach the medical instrument to the adapter. The adapter can be positioned on an instrument drive mechanism. The instrument drive mechanism can be positioned on a robotic arm.

In a first aspect, a medical system can include a medical instrument comprising an instrument handle and an elongated body, wherein the instrument handle is configured to attach to an adapter on an instrument drive mechanism. The system can also include an alignment mechanism configured to provide rotational alignment between the medical instrument and the adapter.

The medical system can include one or more of the following features in any combination: (a) wherein the alignment mechanism extends through a longitudinal axis of the instrument handle; (b) wherein the alignment mechanism comprises an alignment structure on the elongated body; (c) wherein the alignment structure comprises a spiral surface on the elongated body; (d) wherein, when the instrument handle is attached to the adapter, a distal surface on the instrument handle opposes a proximal surface on the adapter; (e) wherein the instrument drive mechanism is positioned on a robotic arm; (f) wherein the robotic arm extends from a bed or a cart; (g) wherein the rotational alignment results in at least one locking element being aligned with and inserted into a corresponding pocket; (h) wherein the locking element is positioned on the adapter and the pocket is positioned on the handle; (i) wherein the locking element comprises a ball bearing; and/or (j) wherein the rotational alignment is passive.

In another aspect, a medical system can include a medical instrument configured for use during a robotically-enabled medical procedure. The medical instrument can include an elongated body extending between a distal end and a proximal end, the distal end configured to be inserted into a patient during a robotically-enabled medical procedure, and an instrument handle including a proximal face and a distal face, wherein the elongated body extends through the proximal face and the distal face. The distal face can be configured to attach to an adapter on an instrument drive mechanism. The medical system can also include an alignment mechanism configured to provide rotational alignment between the medical instrument and the adapter. The alignment mechanism can include a first alignment structure on the medical instrument, and a second alignment structure on the adapter. As the medical instrument is attached to the adapter, the first alignment structure can engage the second alignment structure to provide the rotational alignment.

The medical system can include one or more of the following features in any combination: (a) wherein, when the instrument handle is attached to the adapter, the alignment mechanism extends through a longitudinal axis of the instrument handle; (b) wherein the first alignment structure comprises a spiral surface on the elongated body, and the second attachment structure comprises a bearing surface within an opening of the adapter; (c) wherein the bearing surface comprises a ball bearing; (d) wherein the instrument drive mechanism is positioned on a robotic arm; (e) wherein the robotic arm extends from a bed or a cart; (f) wherein the rotational alignment results in at least one locking element being aligned with and inserted into a corresponding pocket; (g) wherein the locking element is positioned on the adapter and the pocket is positioned on the handle; (h) wherein the locking element is positioned on the handle and the pocket is positioned on the adapter; (i) wherein the locking element comprises a ball bearing; and/or (j) wherein the rotational alignment is passive.

In another aspect, a robotic system can include a medical instrument comprising an instrument handle and an elongated body, wherein the instrument handle is configured to attach to an adapter on an instrument drive mechanism, and an attachment mechanism configured to secure the instrument handle to the adapter, wherein, when the instrument handle is secured to the adapter, the elongated body of the medical instrument extends through an opening in the adapter.

The robotic system can include one or more of the following features in any combination: (a) wherein the attachment mechanism comprises at least three locking elements that are circumferentially positioned about the instrument handle; (b) wherein the attachment mechanism comprises at least one locking element positioned on the instrument handle that is configured to extend into a pocket on the adapter; (c) wherein the attachment mechanism comprises at least one locking element positioned on the adapter that is configured to extend into a pocket on the instrument handle; (d) wherein the locking element comprises a protruding member; (e) wherein the protruding member comprises a ball bearing; (f) wherein the protruding member comprises hook; (g) wherein the protruding member engages a spring-loaded surface in a pocket; and/or (h) wherein the instrument handle is configured to be top loaded onto the adaptor, such that the elongated body of the instrument extends through the opening in the adapter.

In another aspect, a medical system can include a medical instrument configured for use during a robotically-enabled medical procedure, the medical instrument comprising an elongated body extending between a distal end and a proximal end, the distal end configured to be inserted into a patient during a robotically-enabled medical procedure, and an instrument handle including a proximal face and a distal face, wherein the elongated body extends through the proximal face and the distal face, and wherein the distal face is configured to attach to an adapter on an instrument drive mechanism. The medical system can also include an attachment mechanism configured to secure the medical instrument to the adapter, wherein, when the instrument handle is secured to the adapter, the elongated body of the medical instrument extends along an axis from the distal face through an opening in the adapter, wherein the attachment mechanism comprises at least three locking elements positioned circumferentially about the axis.

The medical system can include one or more of the following features in any combination: (a) wherein at least one of the locking elements comprises a protruding member; (b) wherein the protruding member comprises a ball bearing; (c) wherein the protruding member comprises hook; and/or (d) wherein the protruding member engages a spring-loaded surface in a pocket.

In another aspect, a method includes inserting an elongated body of a medical instrument through an opening of an adapter attached to an instrument drive mechanism; advancing a handle of the medical instrument toward the adapter such that an alignment mechanism provides rotational alignment between the medical instrument and the adapter; and attaching the handle of the medical instrument to the adapter.

The medical system can include one or more of the following features in any combination: (a) wherein the medical instrument includes a spiral surface on the elongated body and the adapter includes a bearing surface in the adapter, and wherein the rotational alignment occurs as the bearing surface contacts the spiral surface; (b) wherein attaching the handle of the medical instrument to the adapter comprises engaging an attachment mechanism between the handle and the adapter; (c) wherein engaging an attachment mechanism comprises receiving a protruding member of the attachment mechanism in a pocket of the attachment mechanism; (d) wherein the protruding member is on the handle and the pocket is on the adapter; (e) wherein the protruding member comprises a ball bearing; (f) wherein the protruding member comprises hook; and/or (g) wherein the protruding member engages a spring-loaded surface in the pocket.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 17A is a perspective view of the medical instrument and the adapter on the drive mechanism in an unattached configuration and illustrates the alignment and attachment mechanisms.

FIG. 17B is a perspective view of a proximal face of the adapter and illustrates an embodiment of a first alignment structure of the alignment mechanism on the adapter and embodiments of locking elements of the attachment mechanism on the adapter.

FIG. 17C is a perspective view of a distal face of a handle of the medical instrument and illustrates a second alignment structure of the alignment mechanism on the medical instrument and embodiments of pockets of the attachment mechanism configured to engage with the locking elements.

FIG. 17D illustrates a view of the distal face of the handle of the medical instrument.

FIG. 18A illustrates a locking element and a pocket of the attachment mechanism in an unattached configuration.

FIG. 18B illustrates the locking element and the pocket in an intermediary position between the unattached configuration and an attached configuration.

FIG. 18C illustrates the locking element and the pocket in the attached configuration.

FIG. 19A is a partially exploded perspective view of the adapter.

FIG. 19B is a perspective view of the adapter illustrating the locking element in an assembled configuration.

FIG. 19C is a cross-sectional view of the adapter illustrating the locking element in an assembled configuration.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
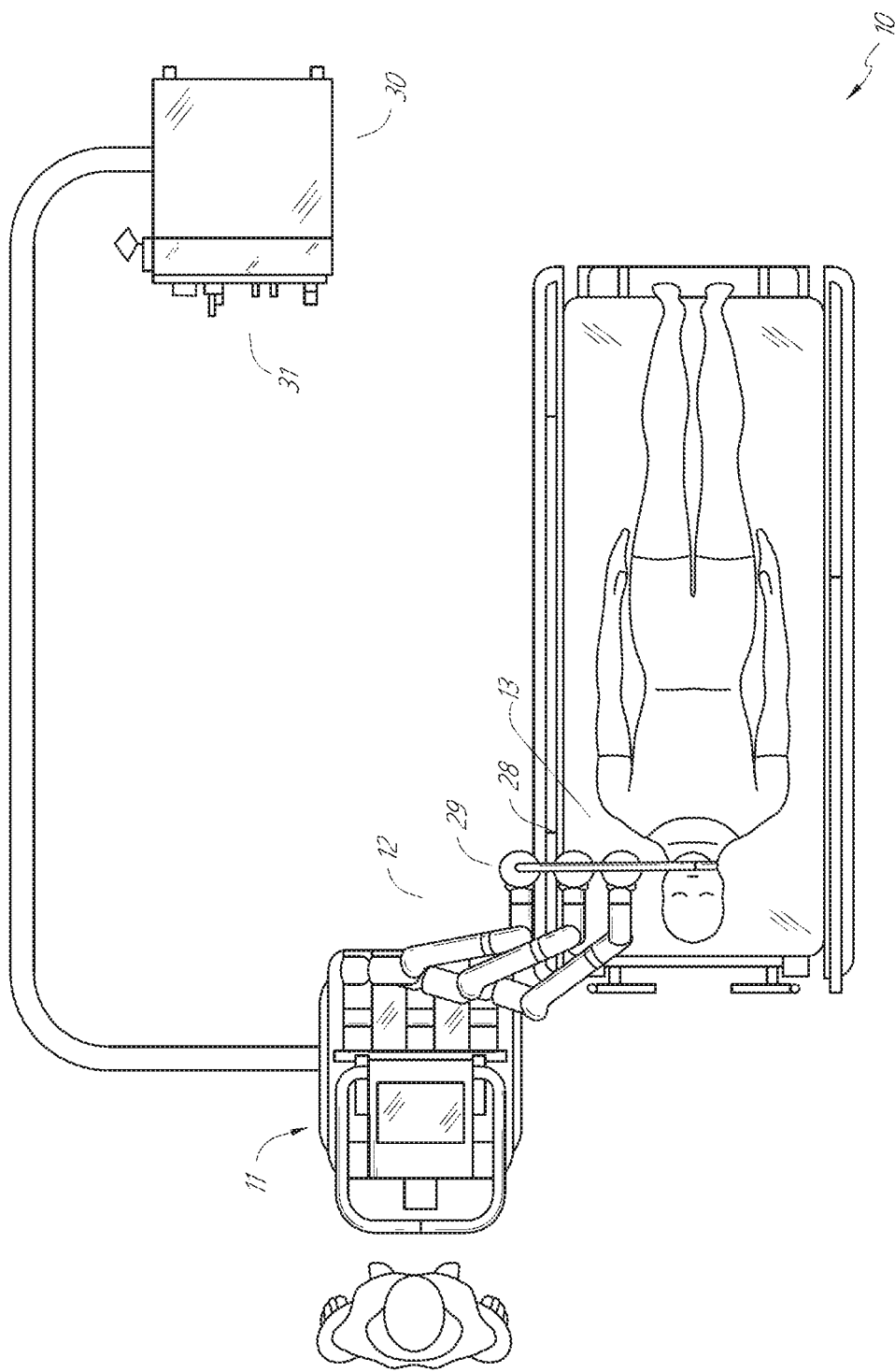
FIG. 1 illustrates an embodiment of a cart-based robotic system arranged for diagnostic and/or therapeutic bronchoscopy procedure(s).
Figure 2:
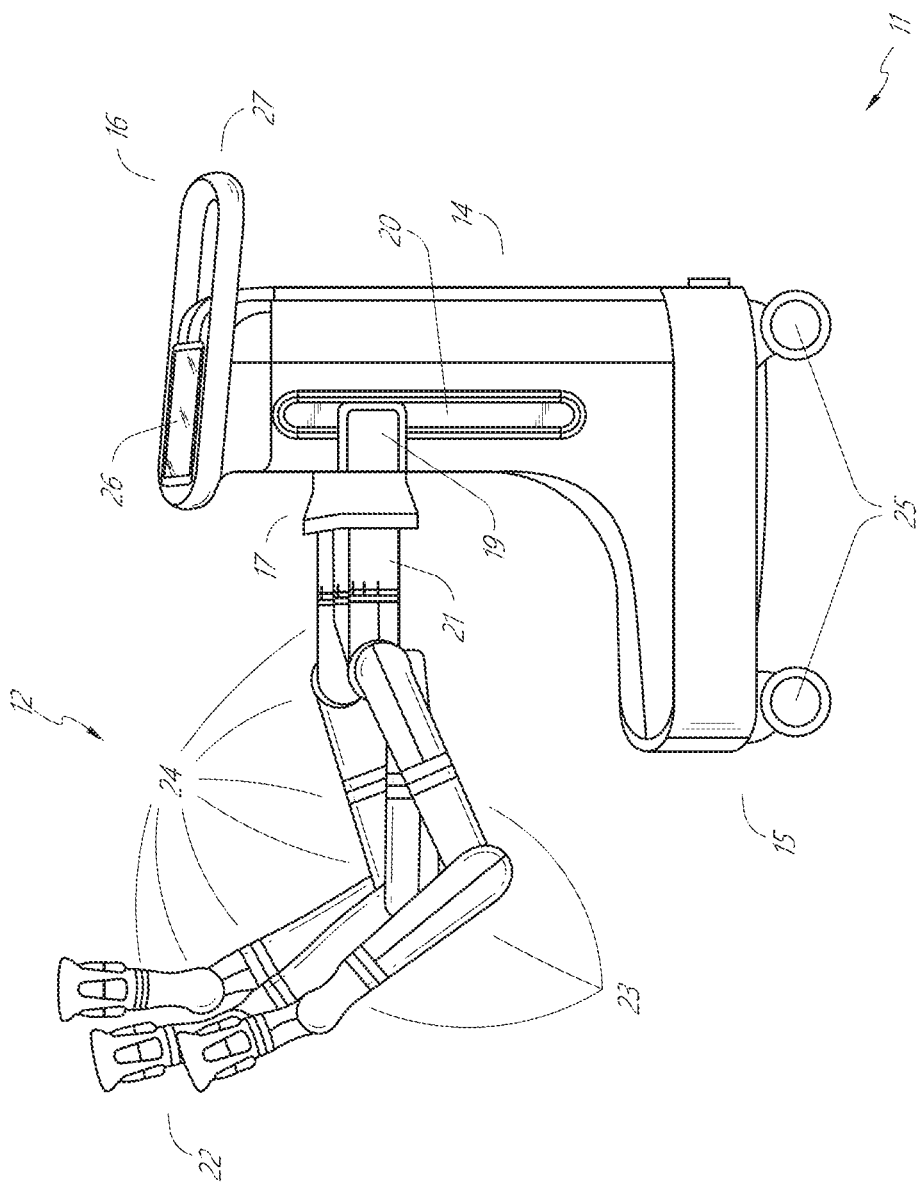
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
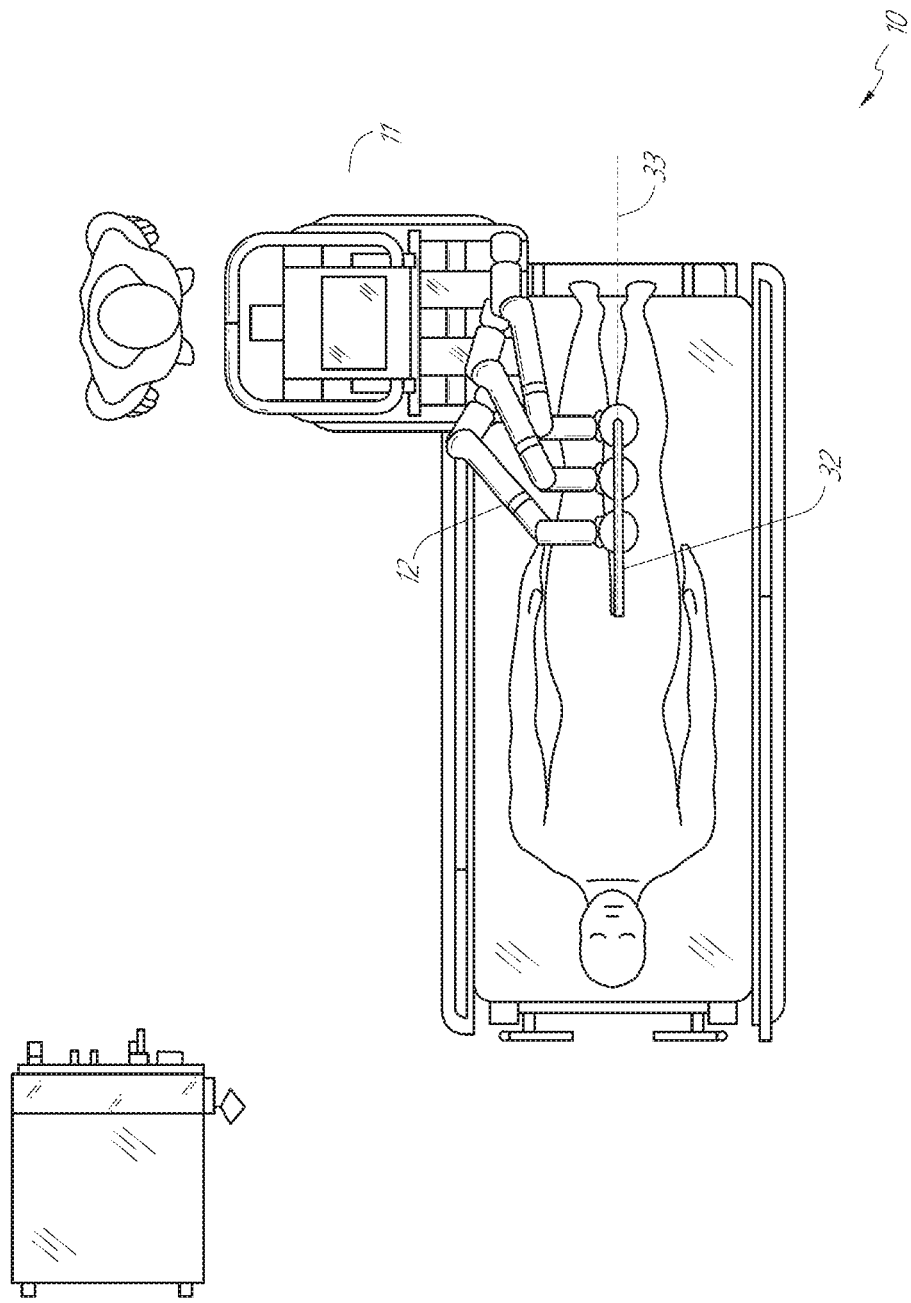
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
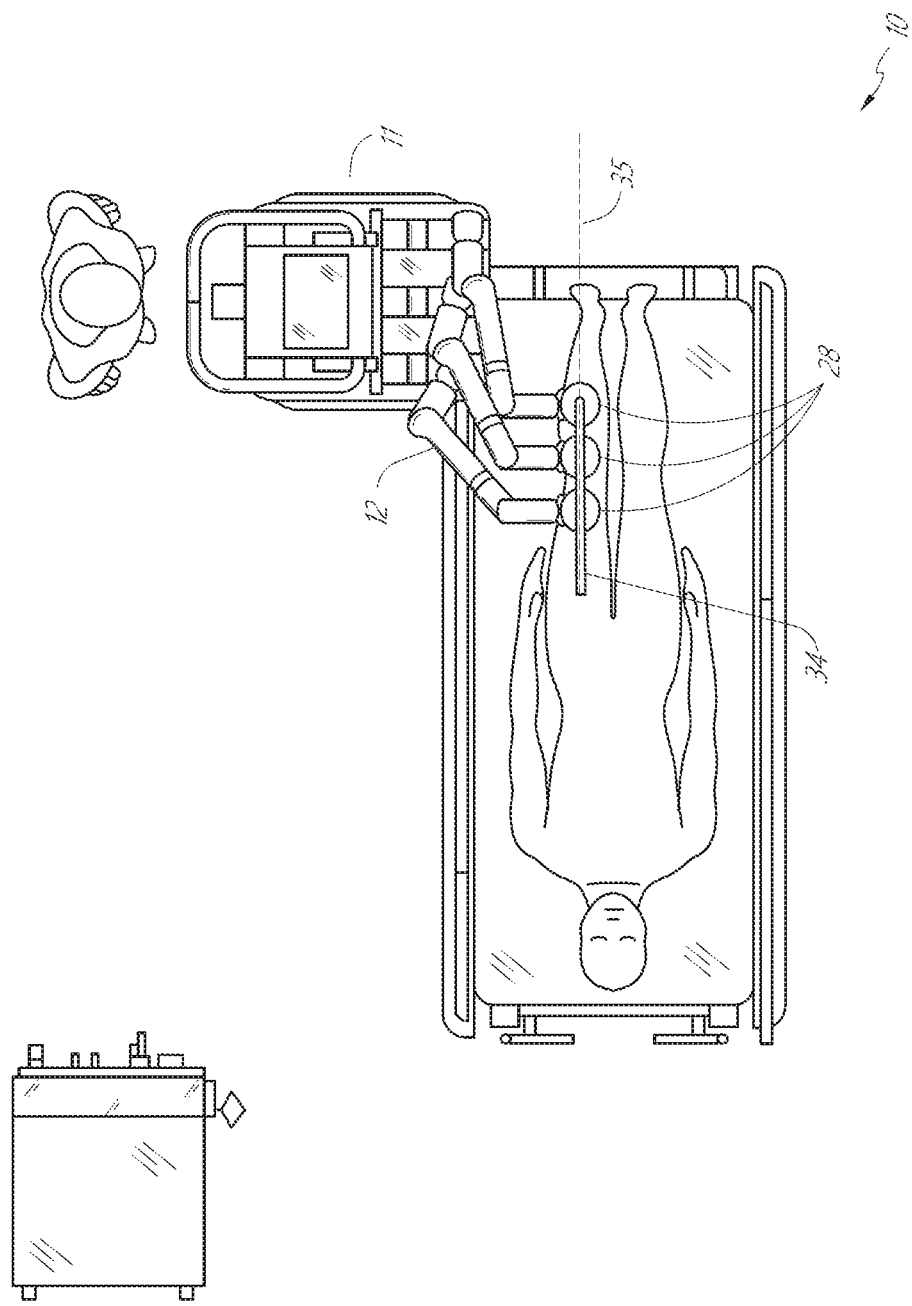
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
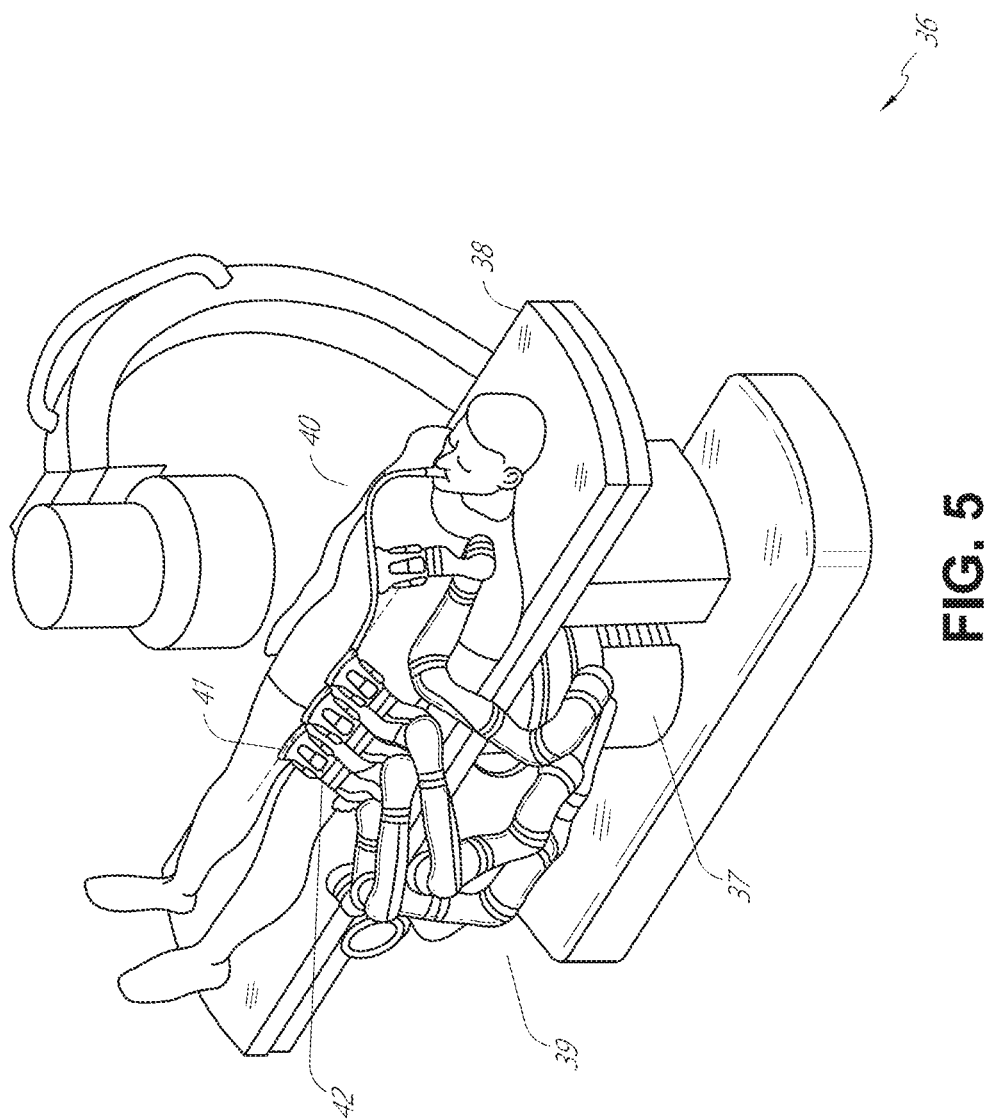
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
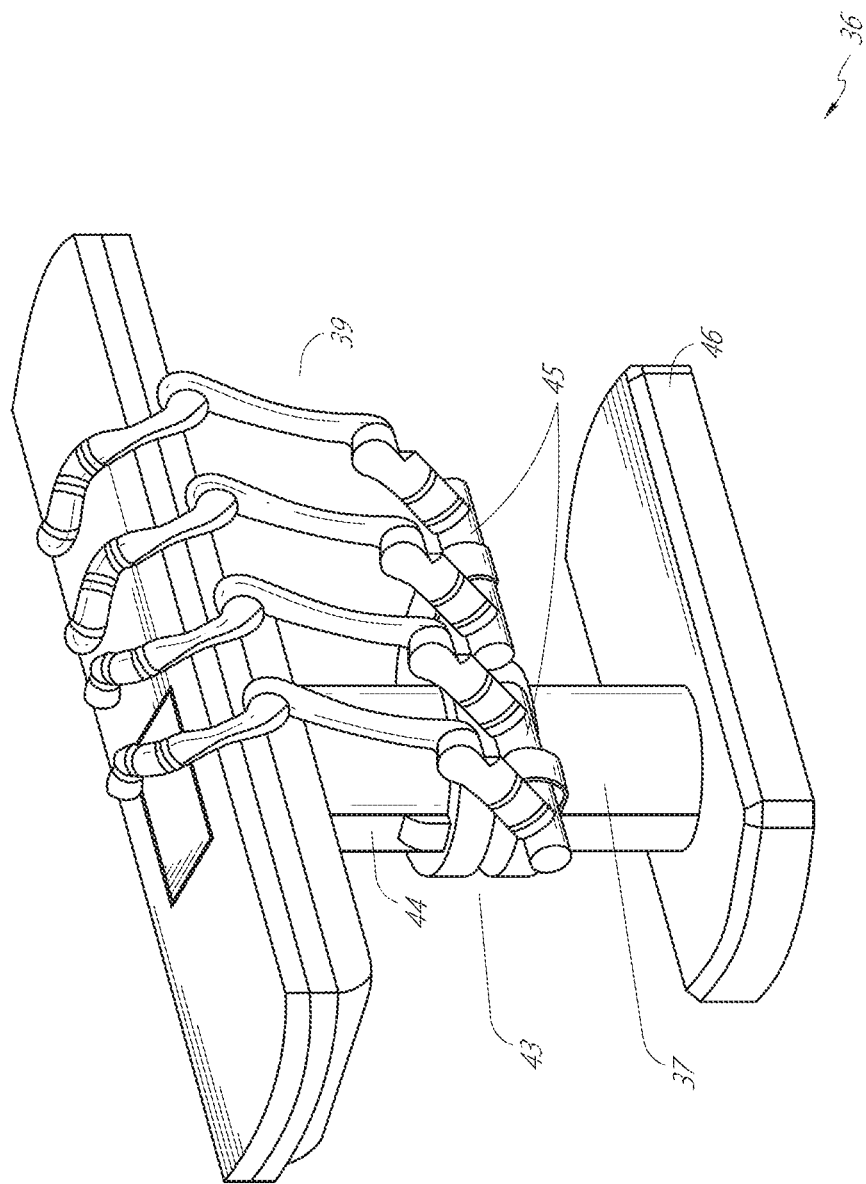
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
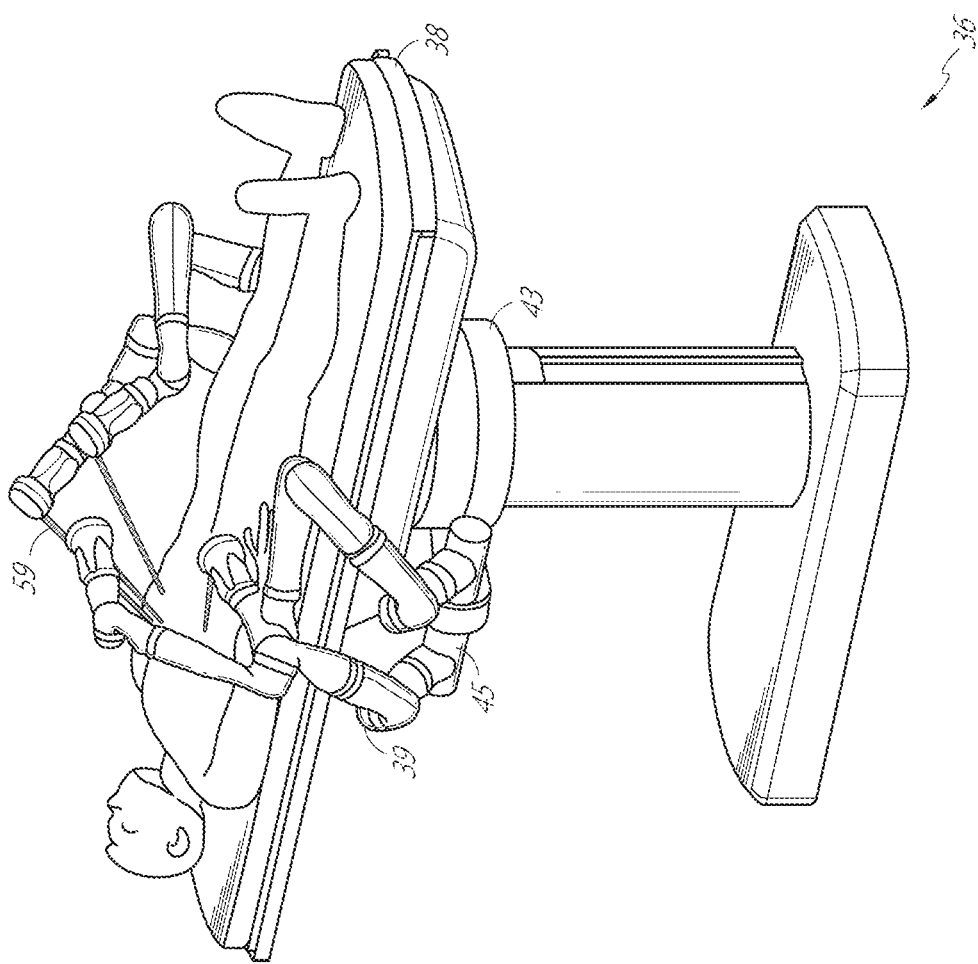
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
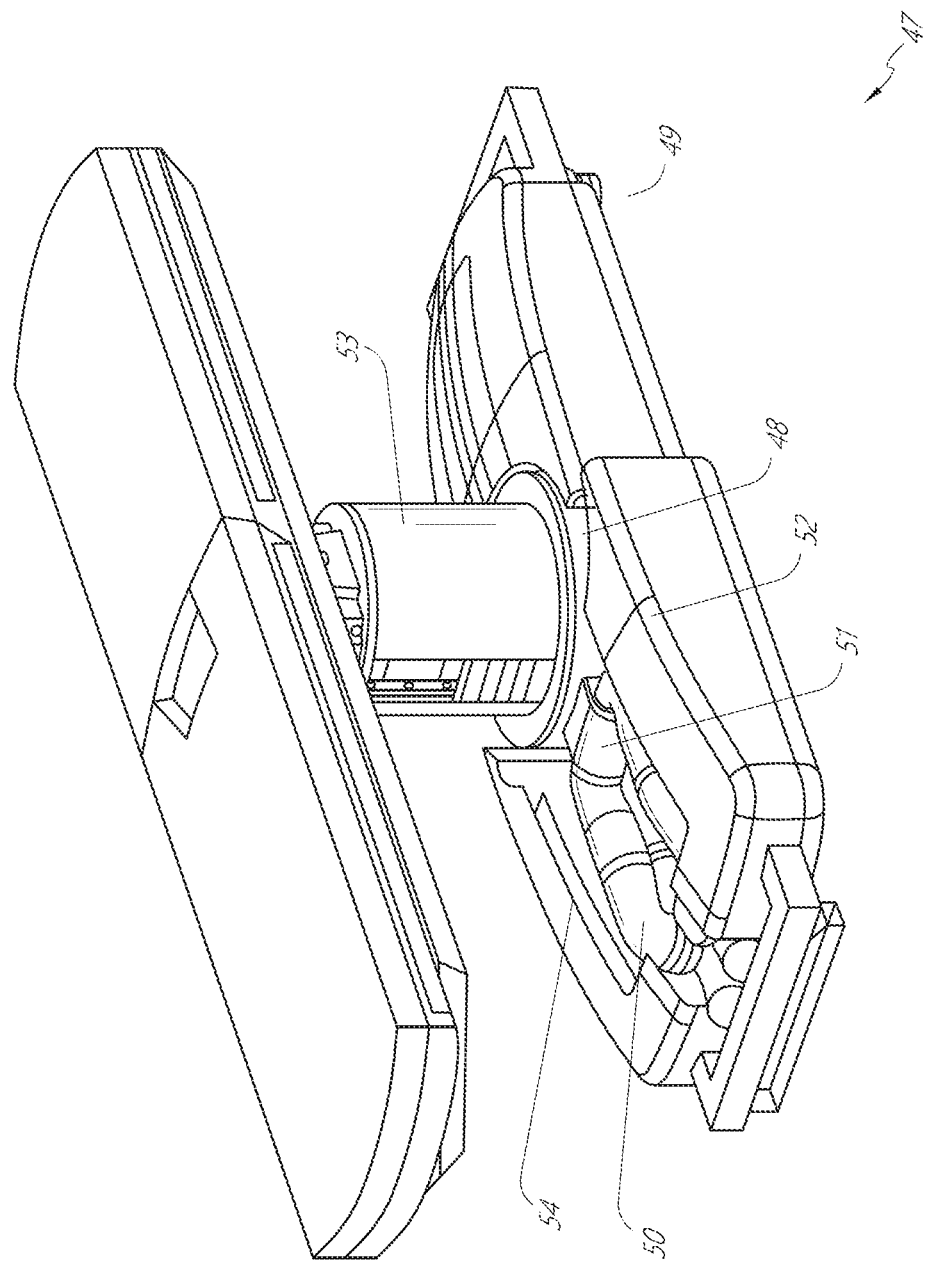
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
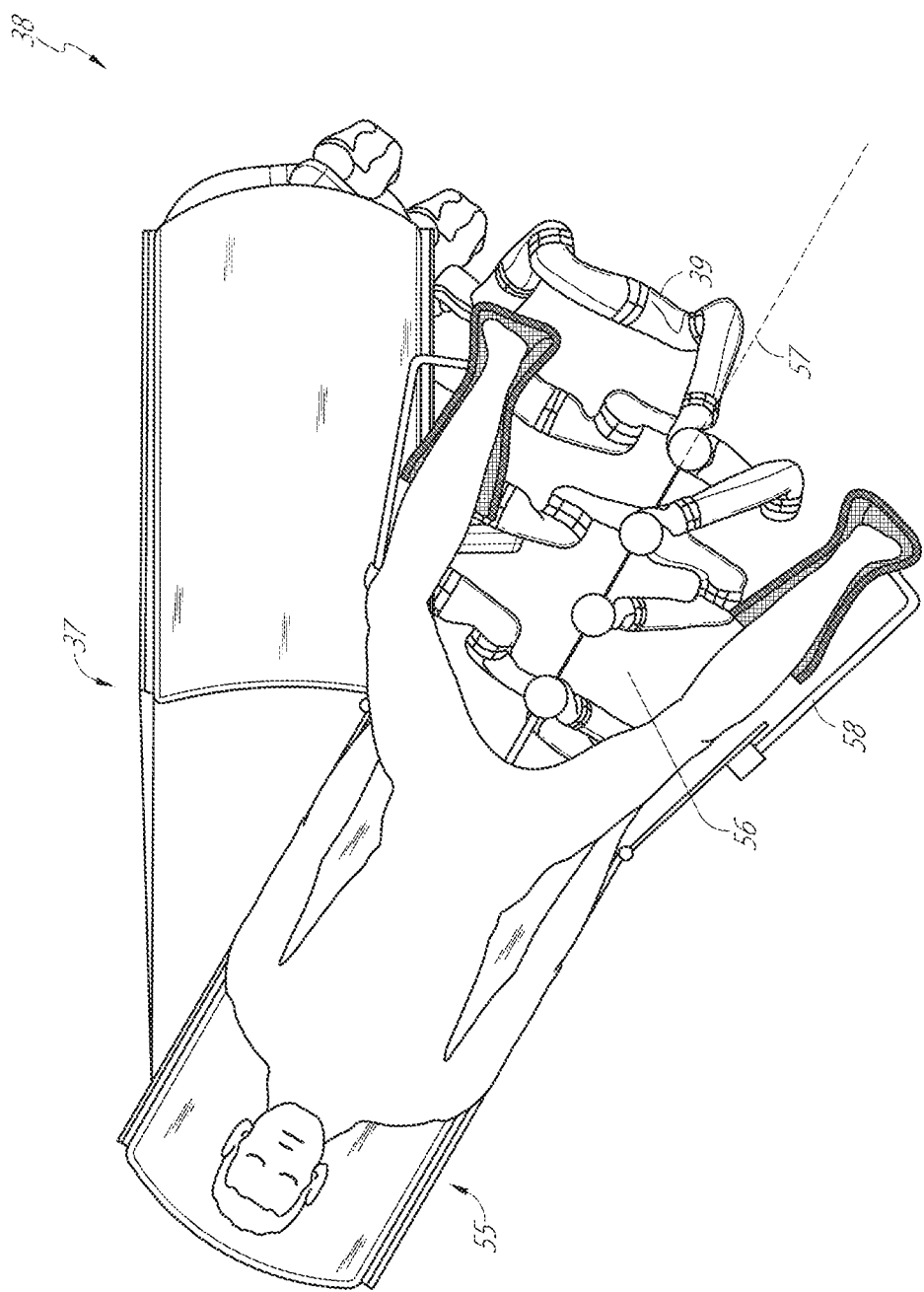
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
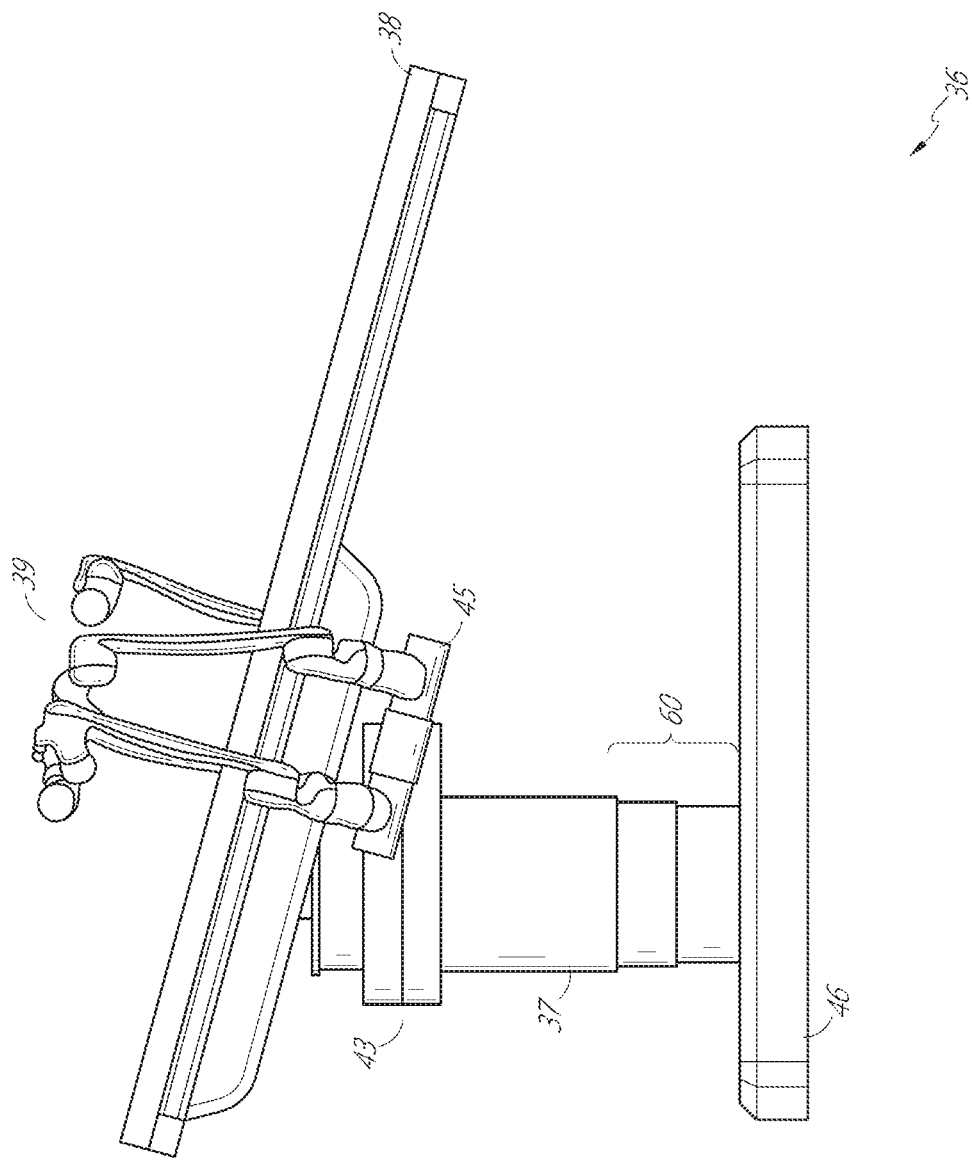
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
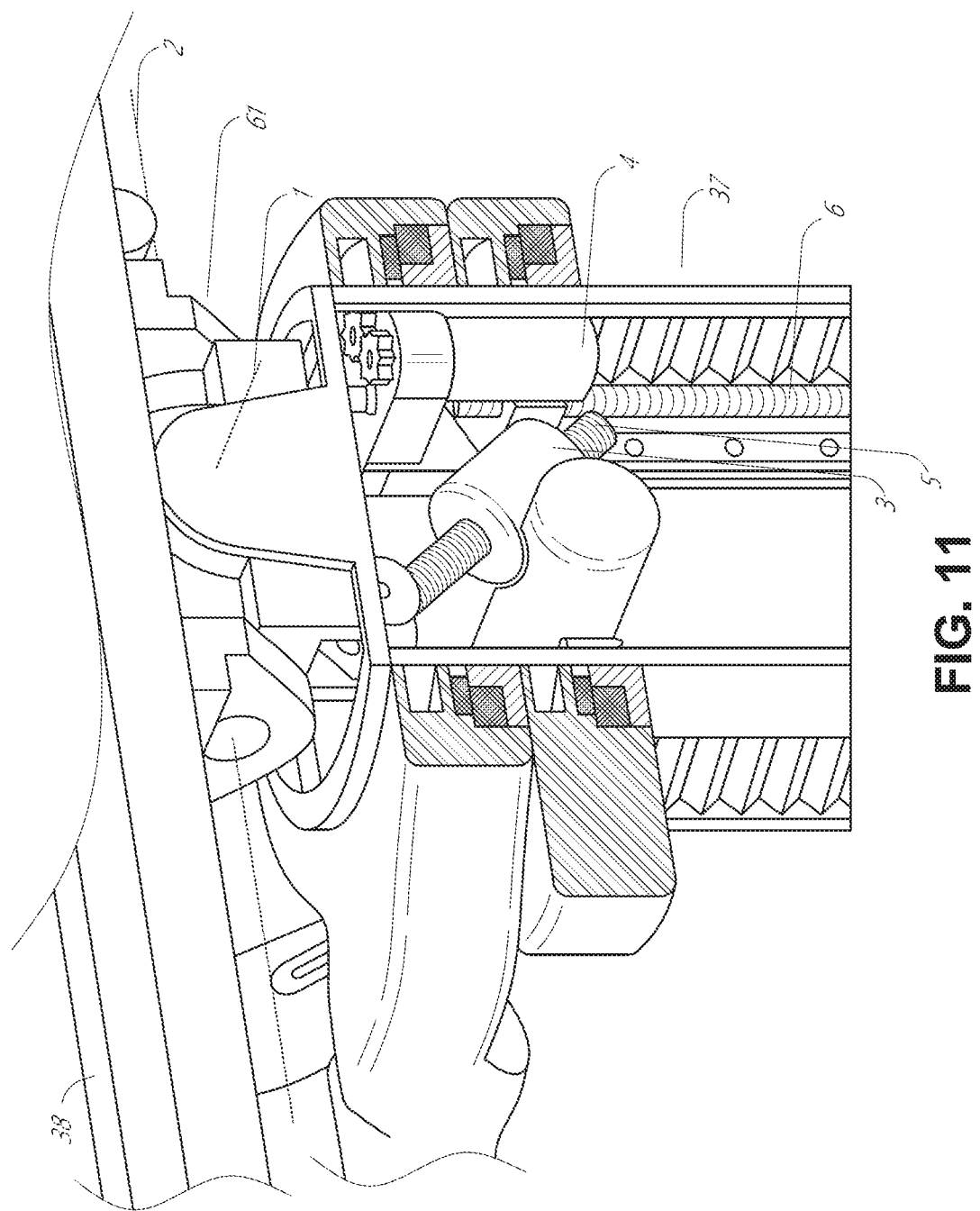
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
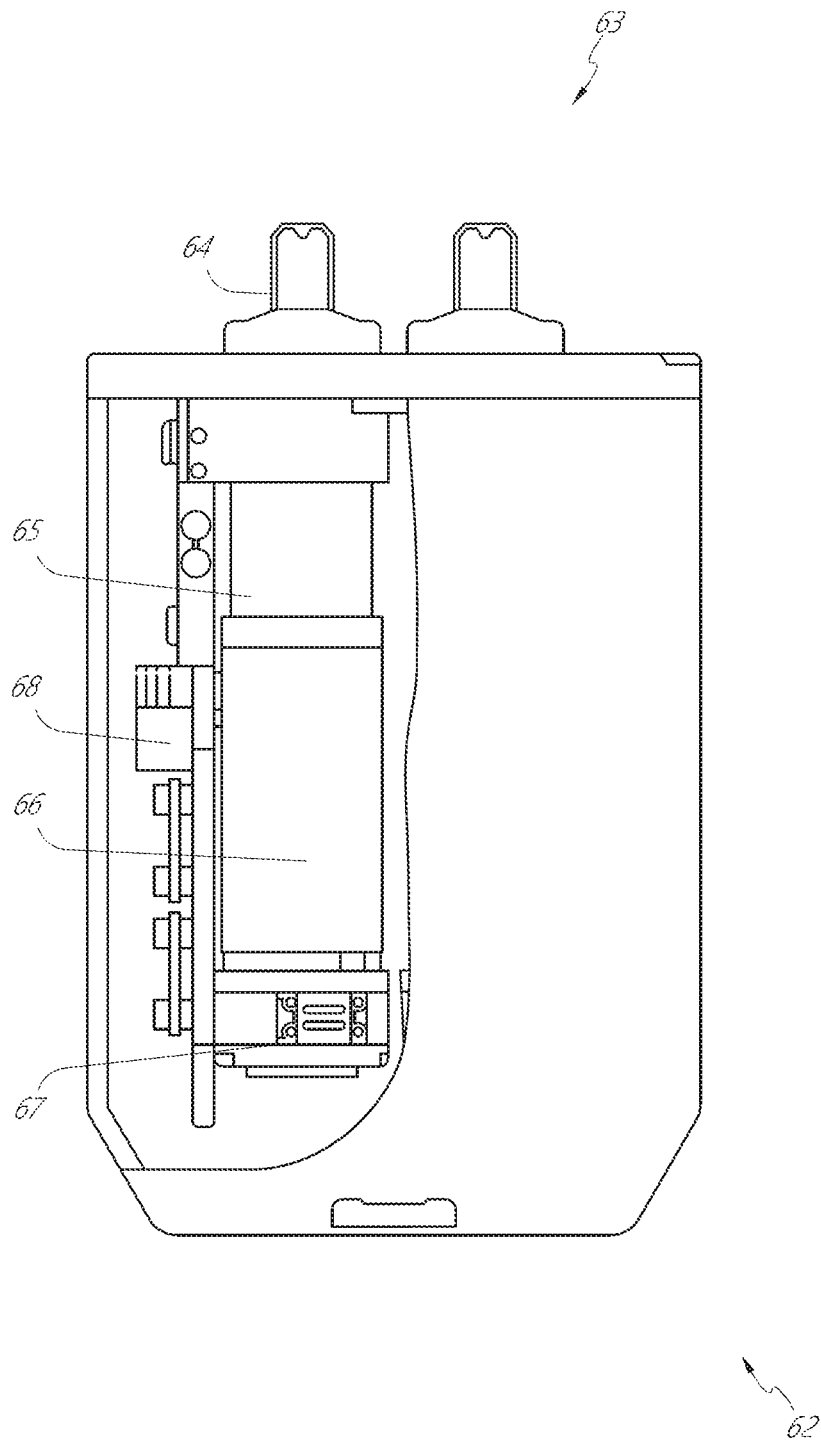
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
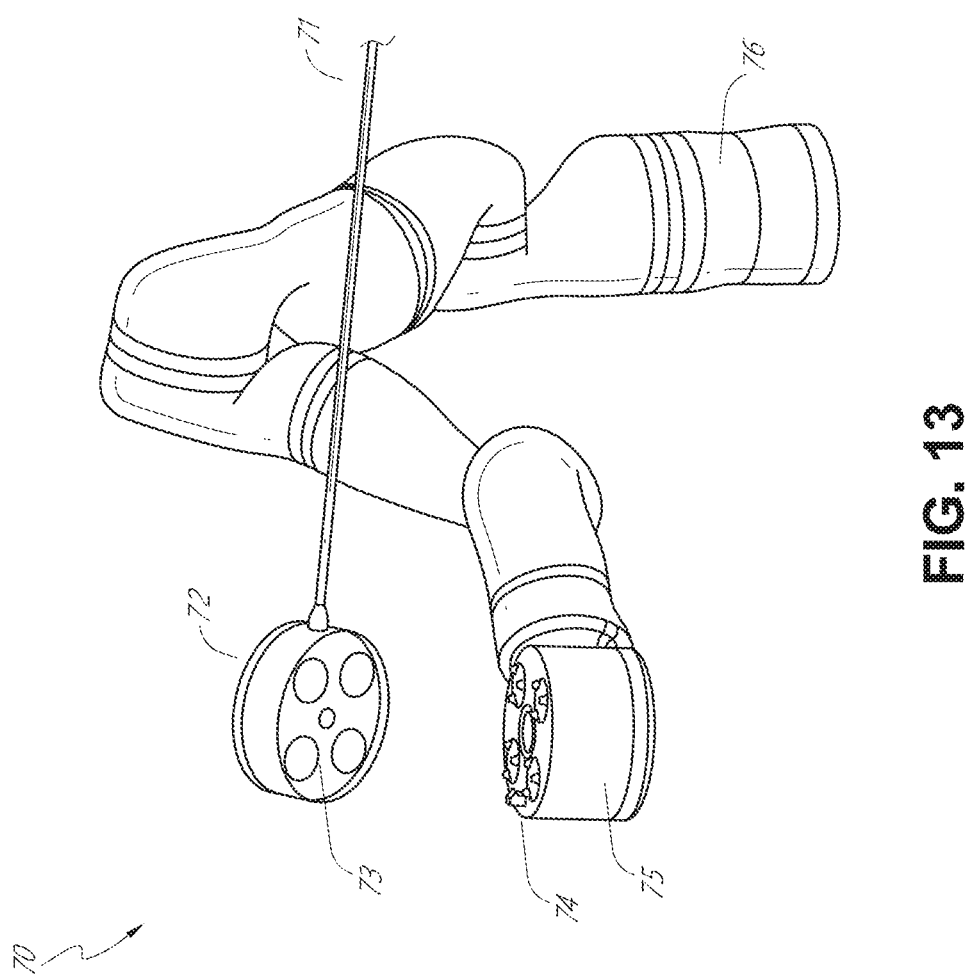
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongated body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 14:
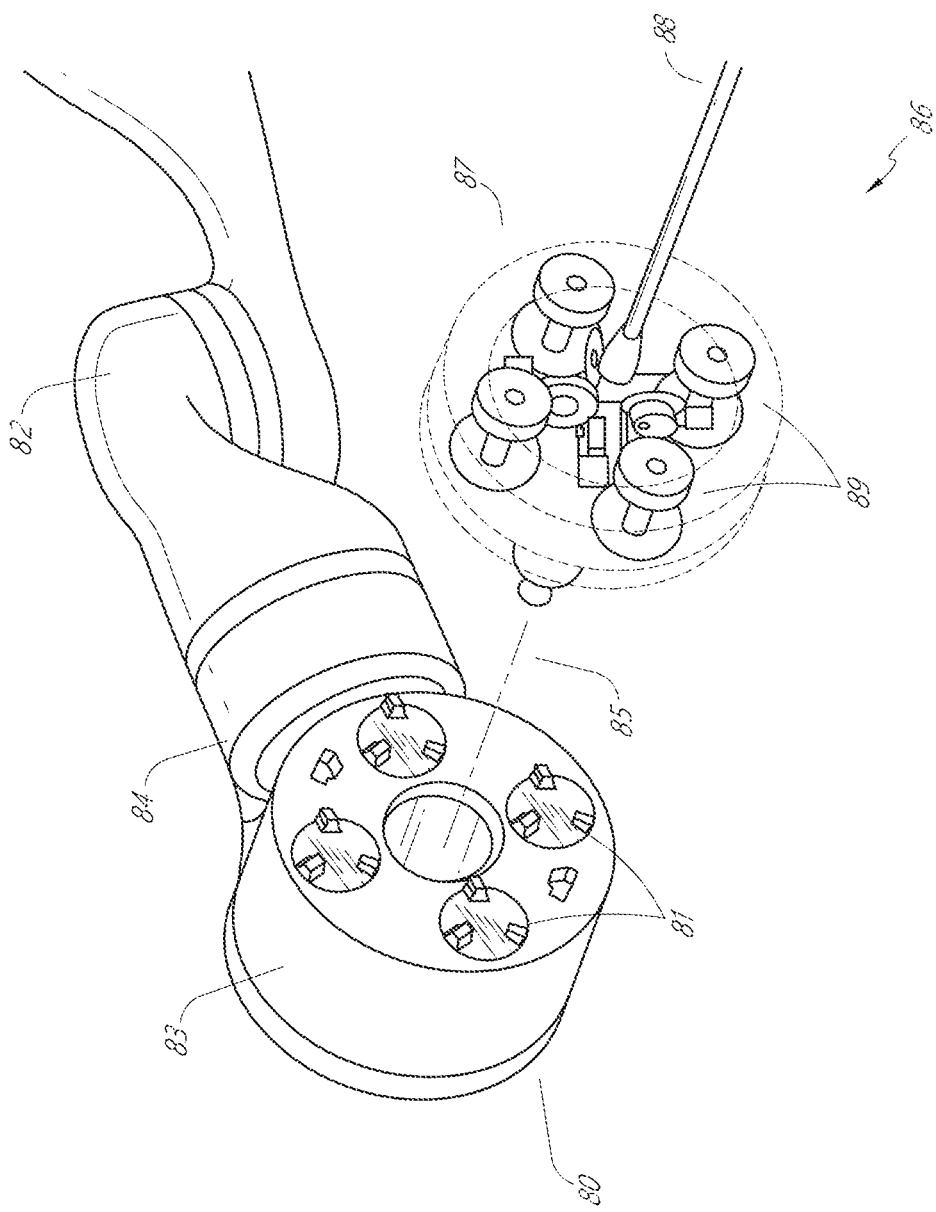
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
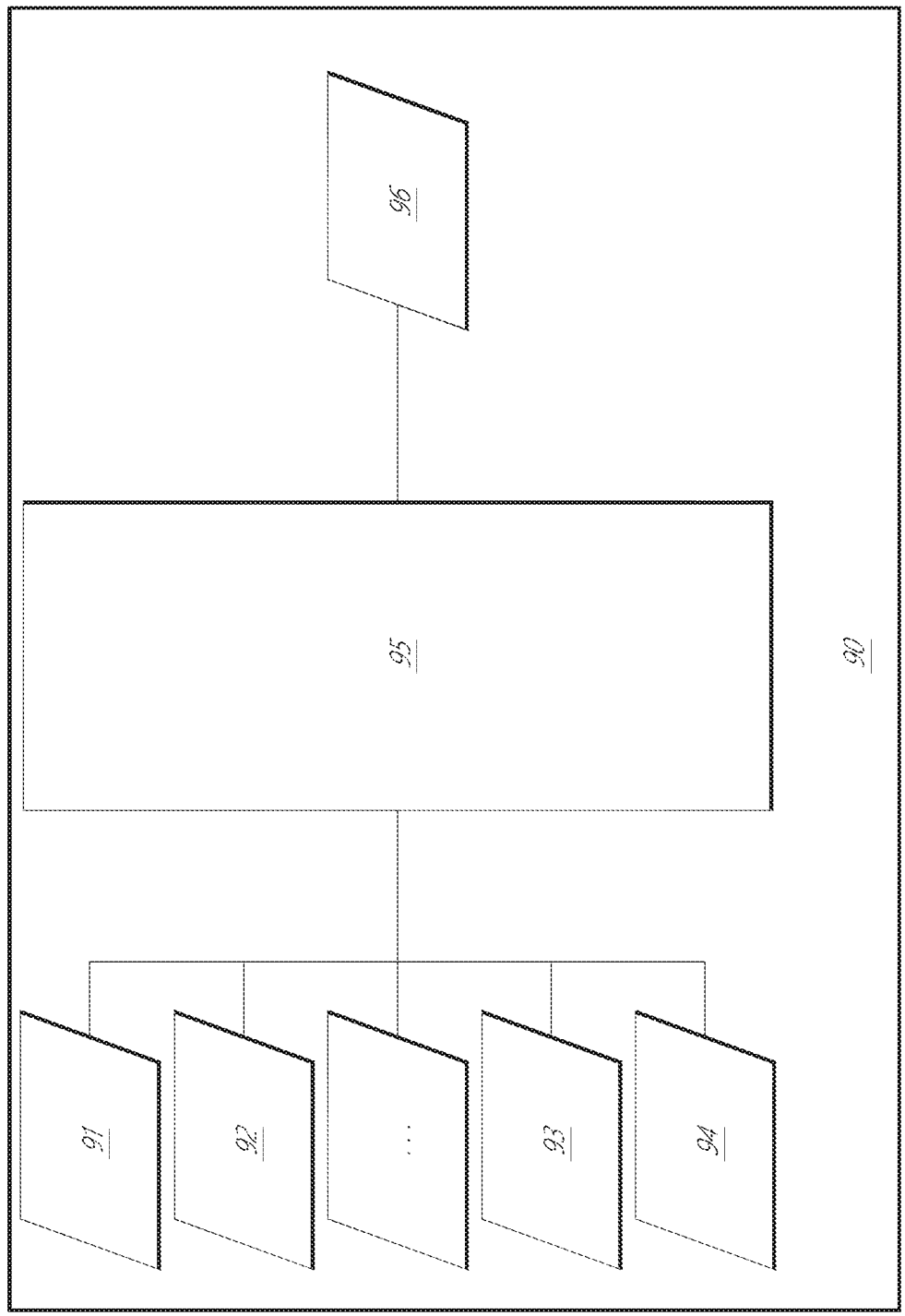
FIG. 15 depicts a block diagram illustrating a localization system that estimates a location of one or more elements of the robotic systems of FIGS. 1-10, such as the location of the instrument of FIGS. 13 and 14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Alignment and Attachment Mechanisms for Medical Instruments

Medical instruments, such as those described above, can include alignment and attachment mechanisms as described in this section. In some embodiments, the alignment and attachment mechanisms provide novel and efficient mechanisms for aligning and attaching an instrument (see, e.g., FIG. 16A) to a robotic arm (see, e.g., FIG. 16B). In some embodiments, the instrument is capable of attaching directly to an instrument drive mechanism of the robotic arm, while in other embodiments, the instrument handle is capable of attaching to an adapter that serves as an interface between the instrument drive mechanism and the instrument. In some embodiments, the adapter helps to maintain sterility in a sterile procedure.

The alignment mechanisms can be configured to facilitate correctly orienting the medical instrument to the component to which the medical instrument will attach. For example, the alignment mechanism can provide proper rotational alignment between the medical instrument and the instrument drive mechanism and/or the adapter. In some embodiments, the alignment mechanism also provides proper translational alignment. Proper alignment between the instrument and the instrument drive mechanism and/or the adapter can facilitate connection of the attachment mechanism. For example, proper alignment can facilitate proper engagement between locking features of the attachment mechanism on the instrument with corresponding locking features of the attachment mechanism on the instrument drive mechanism and/or the adapter.

The attachment mechanisms can be configured to provide a secure and stable connection between the medical instrument and the instrument drive mechanism and/or the adapter. As will be described in more detail below with reference to certain example embodiments illustrated in the figures, the attachment mechanisms can provide circumferential locking with multiple points of connection. For example, in some embodiments, the attachment mechanism comprises two, three, four, five, or more locking features that can be positioned circumferentially around an axis of the instrument, instrument drive mechanism, and/or the adapter. In some embodiments, the instrument comprises a through-loaded instrument that includes an elongated body that extends along an axis that is through-loaded through a channel, bore, or other opening in the instrument drive mechanism and/or the adapter. The attachment mechanism can include locking features positioned on a handle of the instrument circumferentially around the axis of the elongated body. The attachment mechanism can also include corresponding locking features positioned on the instrument drive mechanism and/or the adapter circumferentially around the channel, bore, or other opening.

As will become more fully apparent from the following description, in some embodiments, an advantage of the alignment and attachment mechanisms described herein is that the mechanisms provide improved or increased attachment strength for the instruments. In some embodiments, the mechanisms described herein provide that the instrument is very securely attached and the attachment is stable and/or stiff. Further, in some embodiments, the mechanisms are configured to provide this stable attachment using a limited or minimal number of machined and metal components. This can reduce manufacturing cost and simplify manufacturing processes.

In addition, in some embodiments, the alignment and attachment mechanisms described herein can advantageously require a relatively low force to attach and/or release the instrument to and/or from the instrument drive mechanism or adapter when desired. For example, in some embodiments, the instruments can advantageously be removed or attached with one hand. In some embodiments, the instruments can advantageously be removed or attached when the robotic arm is in any position or orientation. Accordingly, attachment and detachment of the instrument can be performed in a controlled and/or ergonomic manner.

In many of the examples described herein, the alignment and attachment mechanisms are described as providing alignment and attachment between the medical instrument and the adapter. However, in some embodiments, the adapter can be omitted, and the alignment and attachment mechanisms can provide alignment and attachment between the medical instrument and the instrument drive mechanism directly, for example, with no intermediary adapter. Further, in some embodiments, the alignment and attachment mechanisms can be configured to provide alignment and attachment between the medical instrument (or even other non-medical instruments) and any other components to which the instrument can be attached. Thus, the illustrated and described embodiments should be understood as merely providing certain non-limiting examples.

Figure 16A:
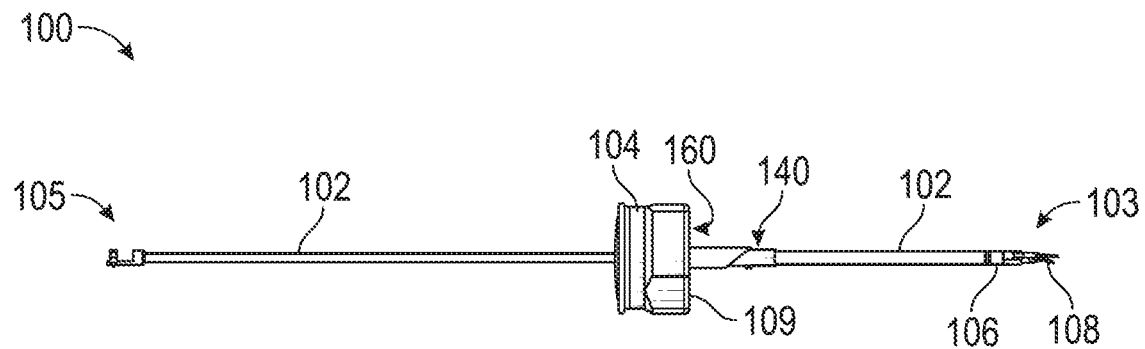
FIG. 16A illustrates an embodiment of a medical instrument that includes an alignment mechanism and an attachment mechanism for aligning the medical instrument with and attaching the medical instrument to an adapter on an instrument drive mechanism.
Figure 16B:
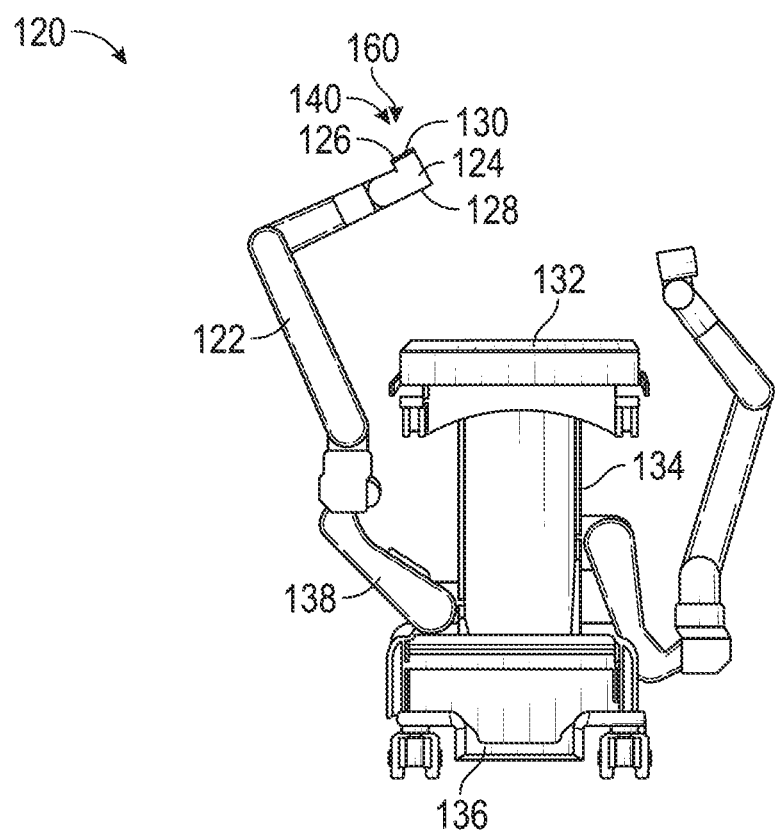
FIG. 16B illustrates an embodiment of an instrument drive mechanism positioned on a distal end of a robotic arm that extends from a bed.

FIG. 16A illustrates an embodiment of a medical instrument 100. FIG. 16B illustrates an embodiment of a medical system 120 that includes robotic arms 122 having instrument drive mechanisms 124 and adapters 126 positioned thereon. As shown in FIGS. 16A and 16B, the medical instrument 100 and the medical system 120 include an alignment mechanism 140 and an attachment mechanism 160. The alignment mechanism 140 is configured to provide proper orientation between the medical instrument 100 and the instrument drive mechanism 124 and adapter 126, and the attachment mechanism 160 is configured to provide a secure connection between the medical instrument 100 and the instrument drive mechanism 124 and adapter 126.

FIG. 16A illustrates a side view of the instrument 100. In the illustrated embodiment, the instrument 100 includes an elongated body 102 and a handle 104. The elongated body 102 extends between a distal end 103 and a proximal end 105. As used herein, the term distal refers to a location or position that is located toward the end of the instrument that is inserted into or otherwise interacts with a patient during a procedure, and the term proximal refers to a location or position that is located in the opposite direction, away from the end of the instrument that is inserted into the patient.

As shown, an end effector 108, which in the illustrated embodiment is configured as a grasper, can be positioned at the distal end 103 of the elongated body 102. In other embodiments, the instrument may include other types of end effectors, such as scissors, clippers, ligation tools, cauterizing tools, basketing tools, etc. In some embodiments, for example, as illustrated, the end effector 108 is connected to the distal end of the elongated body 102 by a wrist 106. The wrist 106 can be configured to allow one or more degrees of freedom for the instrument 100. For example, the wrist 106 can be a two degree-of-freedom wrist. As an example, a two degree-of-freedom wrist can allow the end effector 108 to pivot or rotate around a pitch axis and a yaw axis. In some embodiments, the wrist 106 can be fixed, so as to provide zero degrees of freedom. In some embodiments, the wrist 106 may allow one, two, three, or more degrees of freedom.

As shown in FIG. 16A, the instrument 100 includes the handle 104. The handle 104 can be configured to connect to the instrument drive mechanism 124 or adapter 126 shown in FIG. 16B. As previously mentioned, the instrument 100 may include one or more tendons, cables, or pull wires that extend along (e.g., through or on) the elongated body 102 between the end effector 108 and the handle 104. The handle 104 may include one or more drive inputs configured to engage one or more drive outputs on the instrument drive mechanism (see FIG. 14) that allow the instrument drive mechanism to actuate (e.g., tension or pull) the pull wires. Actuating the pull wires can cause motion of the end effector 108 to allow for remote manipulation and control of the end effector 108. For example, in some embodiments, actuation of the pull wires can be configured to cause jaws of the end effector 108 to open and close and/or to allow the end effector 108 to rotate about pitch or yaw axes. As mentioned above, the instrument drive mechanism can be positioned on a robotic arm 122 (see FIG. 16B). In some embodiments, the robotic arm 122 can be controlled to position, roll, advance, and/or retract the instrument 100.

The elongated body 102 can extend through the handle 104 as illustrated in FIG. 16A. In some such embodiments, the elongated body 102 can be configured to advance or retract relative to the handle 104, although this need not always be the case. In some embodiments, the instrument drive mechanism 124 is configured to cause the elongated body 102 to advance or retract relative to the handle 104. This can allow, for example, the handle 104 to remain stationary while the elongated body 102 and end effector 108 are advanced into a patient during a procedure. In some embodiments, the proximal end of the elongated body 102 is attached to the handle 104 such that the elongated body 102 extends only between the end effector 108 and the handle 104.

As illustrated in FIG. 16A, the handle 104 can include a distal face 109. In some embodiments, the alignment mechanism 140 includes components that extend from the distal face 109. These components can interact or engage with corresponding components of the alignment mechanism 140 on the adapter 126 to provide alignment between the instrument 100 and the adapter 126 when the instrument 100 is attached to the adapter 126. In some embodiments, the attachment mechanism 160 includes components that are positioned on the distal face 109 of the handle 104. These components can interact or engage with corresponding components of the attachment mechanism 160 on the adapter 126 to provide a connection between the instrument 100 and the adapter 126. The alignment mechanism 140 and the attachment mechanism 160 are shown in greater detail in the embodiment illustrated in FIGS. 17A-17D, which are described in greater detail below.

As noted above, FIG. 16B illustrates a view of an embodiment of the medical system 120. In the illustrated embodiment, the medical system 120 includes a plurality of robotic arms 122. Each of the robotic arms 122 includes an instrument drive mechanism 124 positioned on a distal end. As illustrated, the instrument drive mechanism 124 includes a distal face 128 and a proximal face 130. Again, the term distal is used to refer to a direction or position toward the patient, and the term proximal is used to refer to a direction or position away from the patient.

In some embodiments, the instrument 100 is configured to be through loaded onto the instrument drive mechanism 124. For example, the instrument drive mechanism 124 can include a channel, bore, or other opening (not visible) extending through the instrument drive mechanism 124 from the proximal face 130 to the distal face 128, and the instrument can be through-loaded (or top loaded) onto the instrument drive mechanism by inserting the distal end 103 of the elongated body 102 through the proximal face 130, through the channel, and out through the distal face 128. The instrument 100 can be then be moved distally until the distal face 109 of the handle 104 contacts and engages with the proximal face 130 of the instrument drive mechanism 124. In some embodiments, the system 120 includes the adapter 126 positioned on the proximal face 130 of the instrument drive mechanism 124. In such embodiments, the distal face 109 of the handle 104 can contact and engage with the adapter 126. As mentioned previously, the adapter 126 may be a sterile adapter configured to maintain sterility between the instrument 100 and the instrument drive mechanism 124. Through-loading or top-loading the instrument 100 in this manner advantageously allows the instrument 100 to be detached from the instrument drive mechanism 124 in a proximal direction, by pulling the instrument 100 away from the patient. This can advantageously improve patient safety as the instrument 100 can be removed in a direction that is away from the patient.

Further, as will be described below, the alignment mechanism 140 on the instrument 100 and the adapter 126 and/or instrument drive mechanism 124 can provide alignment as the instrument is through loaded onto the instrument drive mechanism 124. For example, as the instrument 100 is lowered distally through the instrument drive mechanism 124, alignment features on the instrument 100 engage with alignment features on the adapter 126 or instrument drive mechanism 124. These features can automatically cause the instrument 100 to rotate into the correct rotational alignment with the adapter 126 or instrument drive mechanism 124. In some embodiments, alignment occurs automatically. In some embodiments, alignment occurs passively. Passive alignment can include alignment that occurs naturally as the instrument 100 and adapter 126 or instrument drive mechanism 124 are brought together. In some embodiments, the alignment mechanism 140 also provides translational alignment between the instrument 100 and the adapter 126 or instrument drive mechanism 124. For example, the alignment mechanism 140 can coaxially align an axis of the instrument 100 with an axis of the adapter 126 or instrument drive mechanism 124.

Alignment, provided by the alignment mechanism 140, can facilitate proper orientation of the attachment mechanism 160. For example, the alignment can ensure that locking features of the attachment mechanism 160 on the distal face 109 of the instrument 100 align with corresponding locking features of the attachment mechanism 160 on the proximal face 130 of the adapter 126 or instrument drive mechanism 124 such that these features can engage when the distal face 109 is brought into contact with the proximal face 130. In some embodiments, engagement of these features can occur automatically or passively. As noted above, a more detailed example of the alignment mechanism 140 and the attachment mechanism 160 will be described in greater detail below with reference to FIGS. 17A-17D.

In the illustrated embodiment of FIG. 16B, the system 120 includes a patient platform 132 or bed that is supported from below by a column 134 or other support and a base 136. As shown, in some embodiments, the robotic arms 122 can be attached to the column 134 or base 136 at a position below the patient platform 132. In some embodiments, the robotic arms 122 can be attached to an adjustable arm support 138, and the adjustable arm support 138 can be attached to the column 134 or base 136 at a position below the patient platform 132. This configuration allows the robotic arms 122 to be deployed from a position below the patient platform 132. In some embodiments, the alignment mechanisms 140 and attachment mechanisms 160 described herein are particularly advantageous in these types of systems (for example, as illustrated in FIG. 16B). For example, in some embodiments of the system 120, the instrument drive mechanism 124 allows for the attached instrument 100 to have infinite roll via a motor in the instrument drive mechanism 124, which should be accommodated by the attachment mechanism 160. In addition, the instrument 100 should be able to both rapidly attach and detach from the robotic arm 122.

Figure 17A:
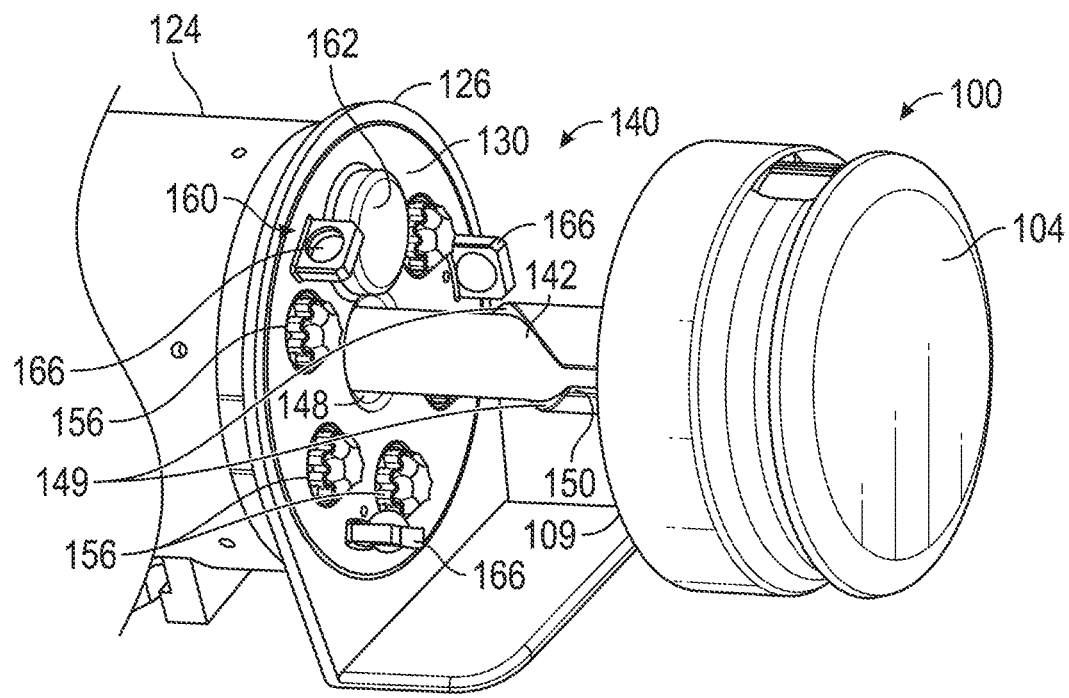
FIGS. 17A-17D provide detailed views of an embodiment of an alignment mechanism and an embodiment of an attachment mechanism for aligning a medical instrument with and attaching the medical instrument to an adapter on an instrument drive mechanism.
Figure 17B:
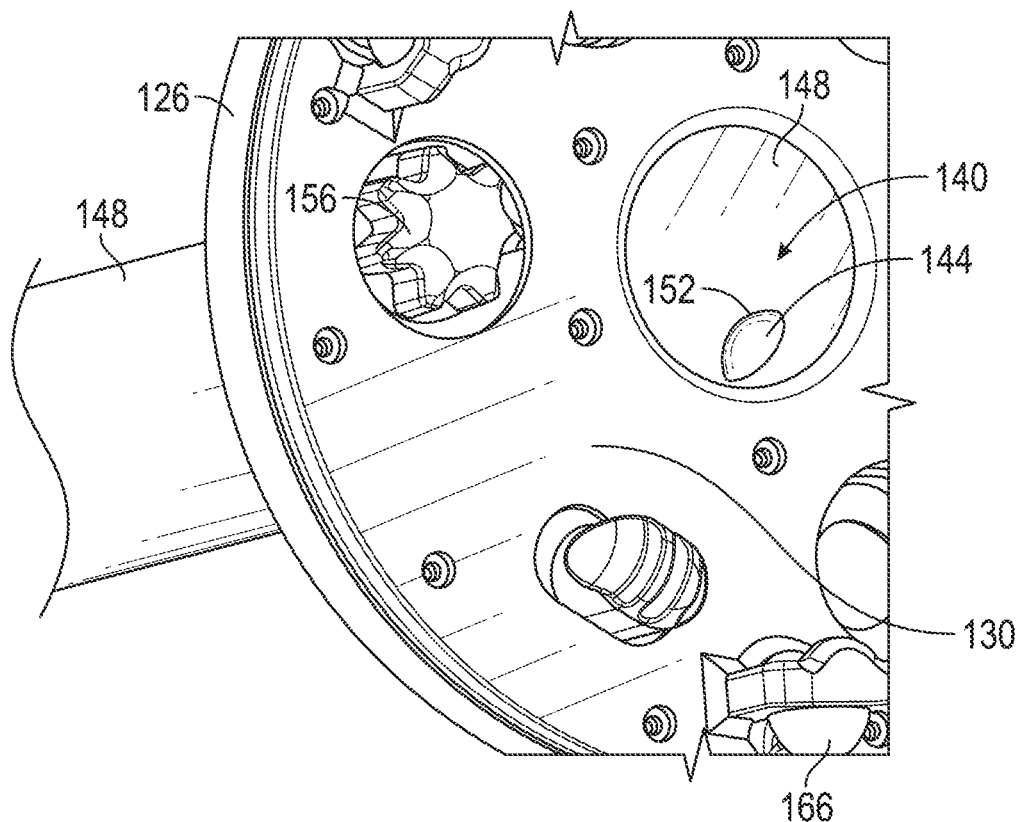
Figure 17C:
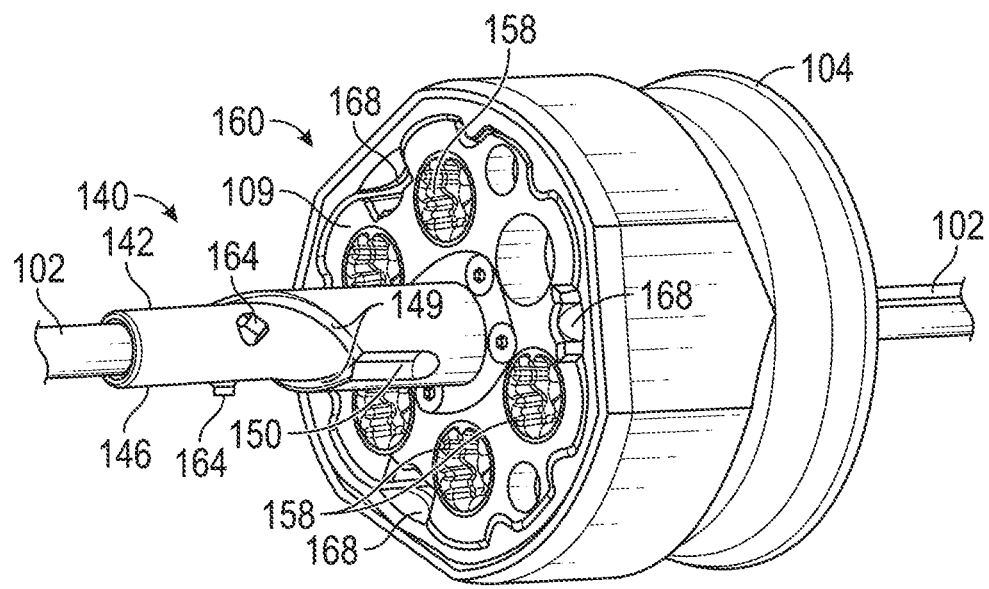
Figure 17D:
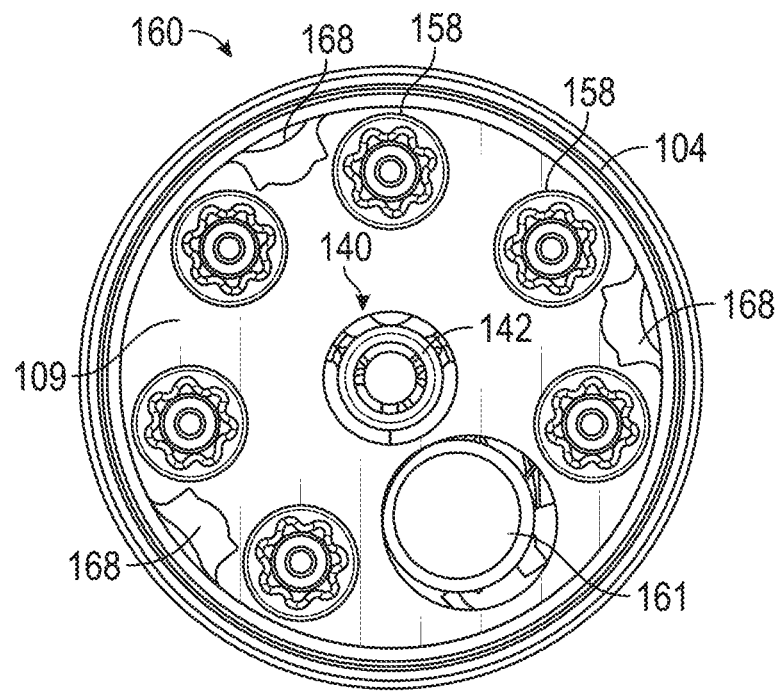

FIGS. 17A-17D provide detailed views of an embodiment of the alignment mechanism 140 and an embodiment of the attachment mechanism 160. FIG. 17A is a perspective view of the medical instrument 100 and the adapter 126 on the drive mechanism 124 in an unattached configuration. FIG. 17B is a perspective view of the proximal face 130 of the adapter 126. FIG. 17C is a perspective view of a distal face 109 of the handle 104 of the medical instrument 100. FIG. 17D illustrates a view of the distal face 109 of the handle 104 of the medical instrument 100. Example alignment mechanisms 140 and attachment mechanisms 160 will be described with reference to these figures in the following sections.

B. Example Alignment Mechanisms

As shown in FIGS. 17A-17D, the instrument handle 104 and the adapter 126 include the alignment mechanism 140. For example, as illustrated, the alignment mechanism 140 can include a first alignment structure 142 on the instrument 100 (see FIGS. 17A and 17C) and a second alignment structure 144 on the adapter 126 (see FIG. 17B). As will be described below, the first alignment structure 142 can be configured to engage or contact the second alignment structure 144 as the instrument 100 is though loaded onto the instrument drive mechanism 124.

As best seen in FIGS. 17A and 17C, in the illustrated embodiment, the first alignment structure 142 comprises a shaft 146 that extends from the distal face 109 of the handle 104. The elongated body 102 of the instrument 100 may extend through the shaft 146 (FIG. 17C). The shaft 146 can have a length that extends from the distal face 109 for a distance that allows the shaft 146 to extend into the channel 148 of the adapter 126 (and/or instrument drive mechanism 124) as shown in FIG. 17A. In some embodiments, the shaft 146 is sufficiently long such that it extends entirely through the instrument drive mechanism 124. In some embodiments, the shaft 146 extends partly through instrument drive mechanism 124.

The first alignment structure 142 also comprises an alignment surface 149 formed on an exterior surface of the shaft 146. As will be described below, the alignment surface 149 engages and contacts the second alignment structure 144 as the instrument 100 is through loaded onto the instrument drive mechanism 124 to provide alignment. In some embodiments, the alignment surface 149 is configured as an angled surface. The angled surface may be formed as a surface that lies in a plane that is not orthogonal to a longitudinal axis of the shaft 146. In some embodiments, the alignment surface 149 is configured as a spiral surface. The spiraled surface may spiral around the longitudinal axis of the shaft 146 in a helical or spiral manner.

In the illustrated embodiment, the first alignment structure 142 also includes an alignment groove 150. The alignment groove 150 is also configured to contact and engage with the second alignment structure 144 to provide alignment between the instrument 100 and the adapter 126 or instrument drive mechanism 124. The alignment groove 150 may extend along and be formed into the exterior surface of the shaft 146. In some embodiments, the alignment groove 150 may extend along the shaft 146 toward the handle 104 starting from the distal most point of the alignment surface 149 (i.e., a point along the alignment surface 149 that is closest to the handle 104). For example, in some embodiments, the alignment surface 149 is angled with respect to the longitudinal axis of the shaft 146 such that a first portion of the alignment surface 149 is positioned proximally relative to a second portion of the alignment surface 149 that is positioned distally. The groove 150 may extend toward the handle 104 from the second portion of the alignment surface 149.

As illustrated in FIG. 17B, the adapter 126 includes the second alignment structure 144. The second alignment structure 144 can include a protrusion 152 extending from an inner wall of the channel 148. In some embodiments, the protrusion 152 can be integrally formed with the inner wall of the channel 148. In some embodiments, the protrusion 152 can be formed as a separate piece attached to or extending through the inner wall of the channel 148. In some embodiments, the protrusion 152 comprises a portion of a ball bearing that extends through the inner wall of the channel 148. The protrusion 152 contacts and interacts with the alignment surface 149 and alignment groove 150 as the instrument 100 is through loaded onto the adapter 126 to provide alignment between the instrument 100 and the adapter 126.

For example, the adapter 126 can be attached to the proximal face of the instrument drive mechanism 124. The distal end 103 of the elongated body 102 of the instrument 100 can be inserted into the channel 148 through the proximal face 130 in the adapter. The instrument 100 is moved in a distal direction bringing the distal face 109 of the handle 104 toward the proximal face 130 of the adapter 126. Eventually, the shaft 146 of the first alignment structure 142 enters the channel 148. Inserting the shaft 146 of the first alignment structure 142 into the channel 148 can provide translational alignment between the instrument 100 and the adapter 126; however, at this stage, the instrument 100 may not be properly rotationally aligned with the adapter 126. As the instrument 100 is moved further in the distal direction, the protrusion 152 of the second alignment structure 144 is brought into contact with the alignment surface 149 of the first alignment structure 142. The protrusion 152 rides along the alignment surface 149 causing the instrument 100 to rotate into the correct orientation. In some embodiments, the causes passive, automatic, or natural alignment. The protrusion 152 eventually reaches the distally lowest most point of the alignment surface 149. At this point the instrument 100 is in the proper rotationally aligned position. This allows the protrusion 152 to enter the alignment groove 150. The alignment groove 150 is sufficiently narrow such that further rotation of the instrument 100 is limited or prohibited. The instrument 100 can then be moved all the way in the distal direction until the distal face 109 of the handle 104 contacts the proximal face 130 of the adapter.

In the aligned position, various features of the instrument handle 104 are aligned with corresponding features of the adapter 126 (and/or instrument drive mechanism 124). These features can include, for example, the corresponding locking features of the attachment mechanism 160 described in greater detail below. The aligned features can also include, for example, drive outputs 156 (see FIGS. 17A and 17B) on the adapter 126 or instrument drive mechanism 124 that are configured to engage with corresponding drive inputs 158 (see FIGS. 17C and 17D) on the instrument handle 104. The drive outputs 156 can engage the drive inputs to control the instrument 100 as described above with reference to FIGS. 13-14. In some embodiments, the drive outputs 156 and drive inputs 158 are configured with a shape that includes some draft (e.g., a cone-like shape) to facilitate alignment and engagement. In the embodiments illustrated in FIGS. 17A-17C, the instrument handle 104 and adapter 126 include five drive outputs 156 and five corresponding drive inputs 158. The embodiment illustrated in FIG. 17D includes six drive inputs 158.

The aligned features can also include, for example, a computer-readable tag, such as RFID tag 161 (see FIG. 17D), on the instrument 100 and a corresponding reader 162 (see FIG. 17A) on the adapter 126 or the instrument drive mechanism 124. In some embodiments, the RFID tag 161 is included on the instrument handle 104 within a channel, recess, or pocket. The RFID tag 161 can be configured to provide a wireless identification of the instrument 100 to the system 120. It can provide parameters to the system 120, and can allow for authentication and tracking of the instrument 100. The reader 162 may be configured to protrude into the channel to access and read the RFID tag 161. In addition, the alignment mechanism 140 can comprise one or more sensors 164 (FIG. 17C). The sensors 164 can be configured to detect the alignment of the elongated body 102 and correctly align it using the infinite roll of the instrument 100.

In some embodiments, the first alignment structure 142 and the second alignment structure 144 can be reversed. For example, the alignment surface 149 and alignment groove 150 can be included within the channel 148 on the adapter 126, and the protrusion 152 can be included on the shaft 146 of the instrument handle 104. Other suitable alignment structures are also possible. For example, other suitable alignment sensors can include key tabs, which may or may not be passive, but will only engage when aligned properly.

As described herein, the instrument handle 104 can include the alignment mechanism 140 to enable the instrument handle 104 to quickly attach to the adapter 126, thereby aligning the attachment mechanism 160 and other components. The alignment mechanism 140 can be in the form of a spiral alignment formed on the instrument shaft. In some embodiments, the alignment mechanism 140 is in the form of a double spiral. The alignment mechanism 140 can quickly align the instrument handle 104 to the adapter 126, thereby providing a quick connect feature that allows for easy exchange of instruments 100 on the robotic arms 122.

B. Example Attachment Mechanisms

As shown in FIGS. 17A-17D, the instrument handle 104 and the adapter 126 include the attachment mechanism 160. For example, as illustrated, the attachment mechanism 160 can include locking elements 166 on the adapter 126 or instrument drive mechanism 124 (see FIGS. 17A and 17C) and corresponding pockets 168 on the instrument 100 (see FIGS. 17C and 17D). As will be described below, locking elements 166 are configured to be received within and engage with the pockets 168 to attach the instrument handle 104 to the adapter 126. As discussed above, the alignment mechanism 140 is configured to facilitate alignment of these features.

As shown in FIG. 17A, the adapter 126 (or the instrument drive mechanism 124) can include the plurality of locking elements 166. In the illustrated embodiment, the adapter 126 includes three locking elements 166, although other numbers of locking elements 166 may be used in other embodiments. For example, the adapter 126 may include two, three, four, five, six or more locking elements 166. The locking elements 166 can extend or project outwardly from the proximal face 130 of the adapter 126.

Advantageously, the locking elements 166 can be positioned circumferentially around the longitudinal axis of the adapter 126. For example, the locking elements 166 can be positioned circumferentially around the channel 148. The locking elements 166, when arranged circumferentially, can provide locking around the perimeter of the adapter 126. This can provide a connection with improved stability over embodiments that includes only a single locking element or locking elements only on a single side of the device. In some embodiments, circumferentially positioned locking elements 166 can be evenly spaced. In some embodiments, the spacing need not be even.

In some embodiments, the locking elements 166 of the adapter 126 comprise radial locking elements. For example, the locking elements 166 can protrude outwardly from the proximal surface of the adapter, and can be configured to engage a spring loaded surface before being received in the pockets 168. Engagement between the locking elements 166 and the pockets can include a radial force that maintains the connection.

Figure 19A:
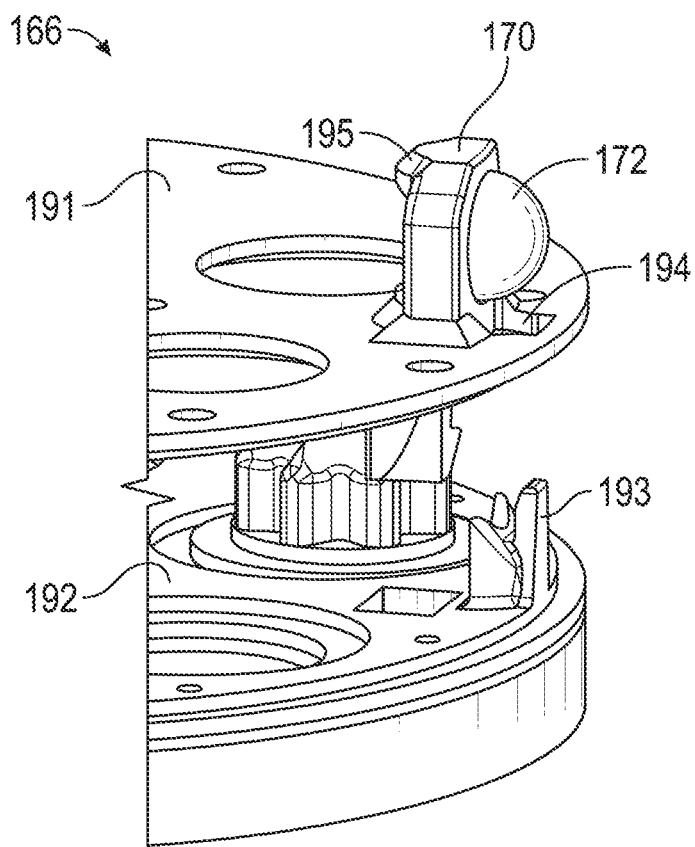
FIGS. 19A-19C provide views illustrating an embodiment of a locking element that includes a ball bearing.
Figure 19B:
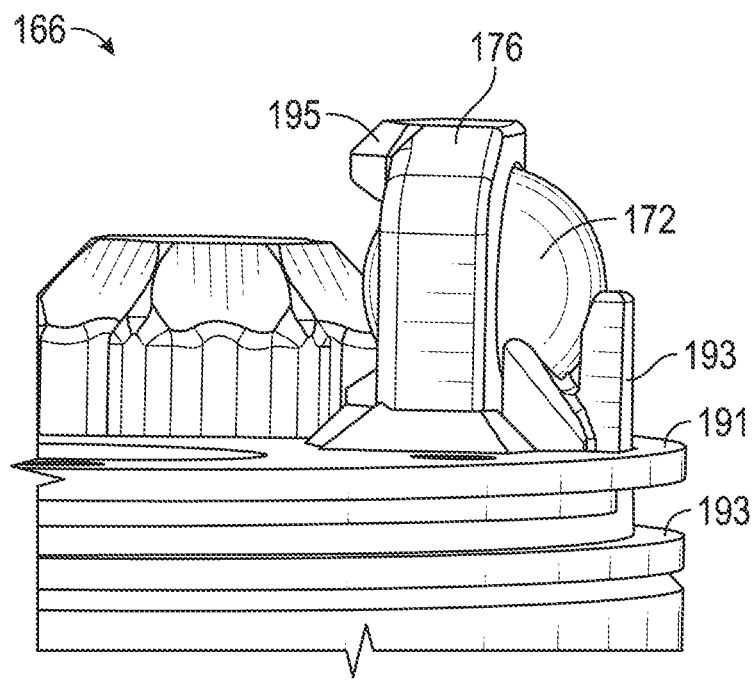
Figure 19C:
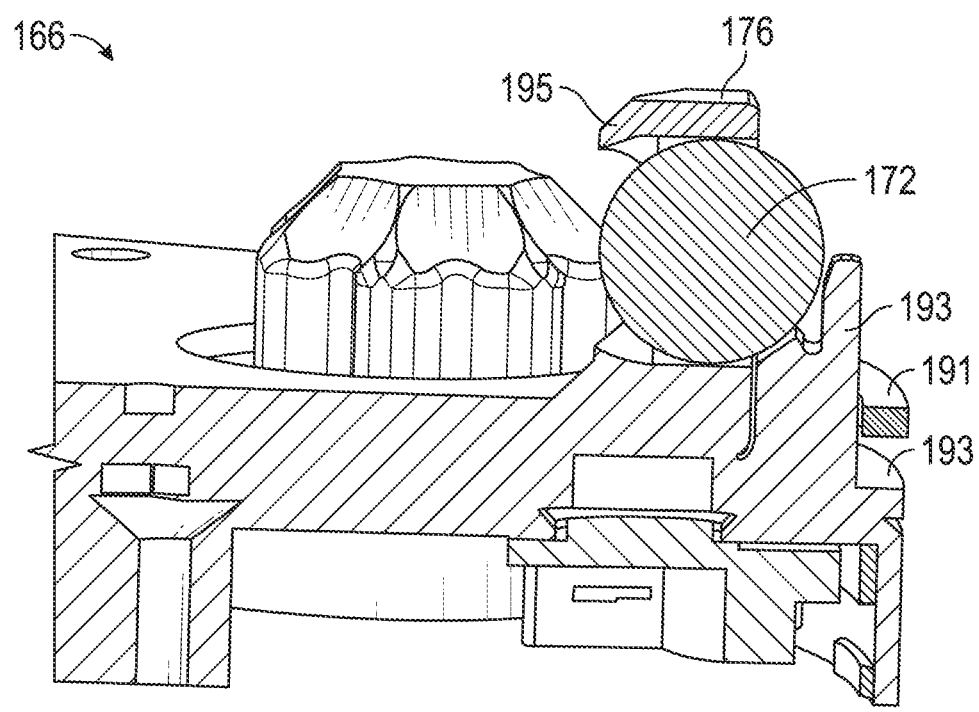
Figure 20:
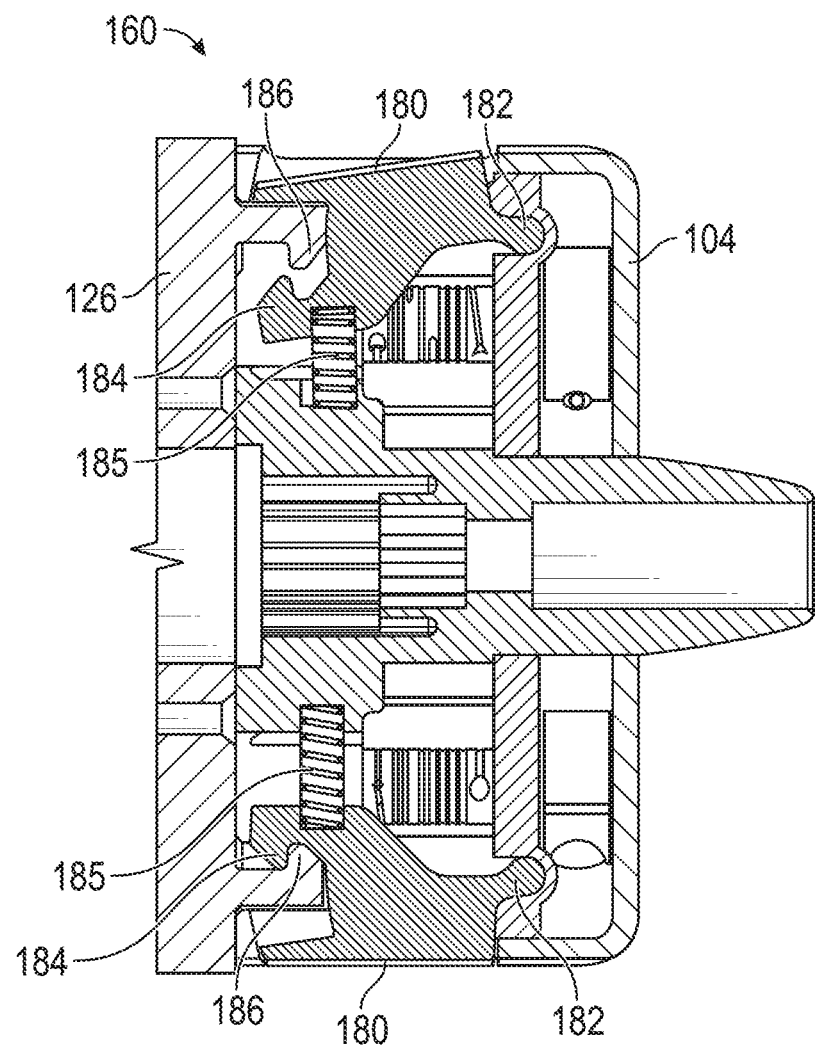
FIG. 20 illustrates another embodiment of an attachment mechanism that includes spring loaded pinch levers.
Figure 21:
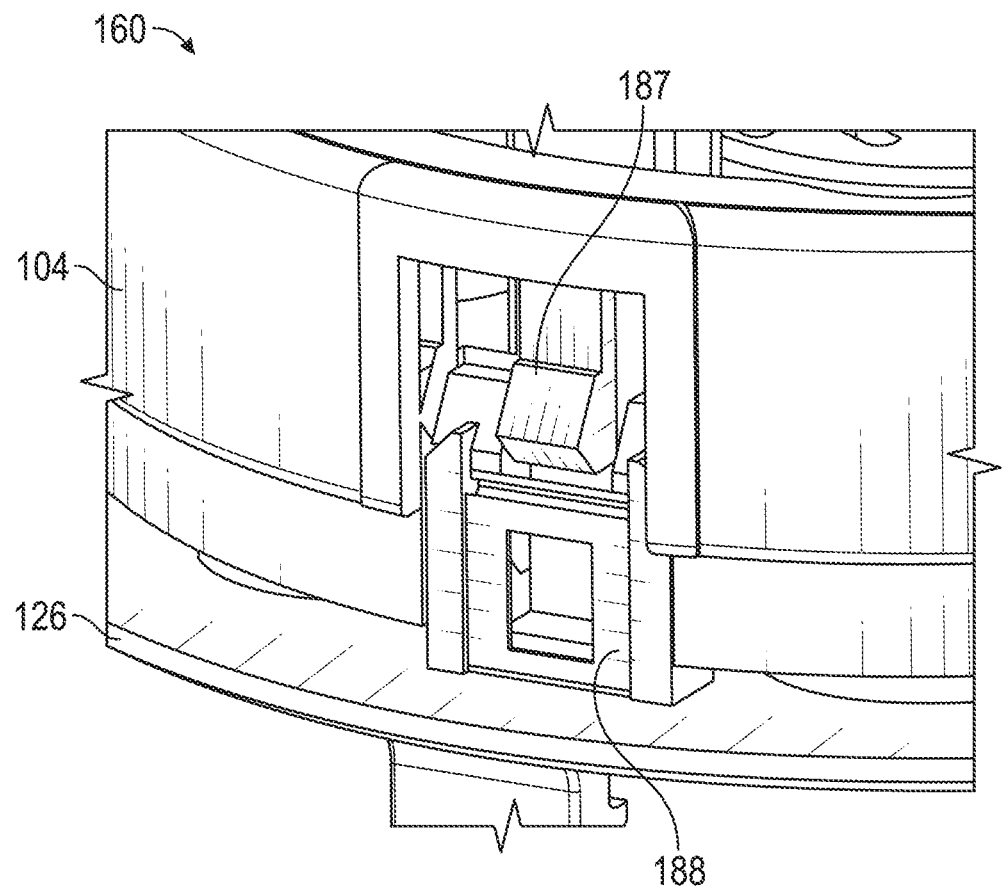
FIG. 21 illustrates another embodiment of an attachment mechanism that includes cantilever hooks.

In the illustrated embodiment of FIGS. 17A-17D, the locking elements 166 comprise a ball bearing. These embodiments are shown in greater detail in FIGS. 18A-19C, which are described below. However, the locking elements 166 can be any type of radial locking element that creates an interlock. In some embodiments, the locking elements can be in the form of a spring tab. Such an embodiment is shown in FIG. 20 described below. In some embodiments, the locking elements 166 can be in the form of a cantilever hook. Such an embodiment is shown in FIG. 21 described below.

As shown in FIGS. 17C and 17D, the distal face 109 of the instrument handle 104 includes pockets 168 configured to receive and engage with the locking elements 166. In the illustrated embodiment, the instrument handle 104 includes three pockets 168 so as to engage with the three locking elements 166 illustrated in FIG. 17A. Of course, other embodiments may include other numbers of pockets 168 so as to correspond with the number of locking elements used on the adapter 126.

In some embodiments, the attachment mechanism 160 not only allows a quick connection between the instrument handle 104 and the adapter 126, but it also allow for easy separation or removal, simply by pulling the instrument handle 104 away from the adapter 126. As mentioned above, the handle 104 is pulled away from the adapter 126 in a proximal direction (away from the patient), which can be advantageous, as there is little to no likelihood that the patient may be accidentally stabbed by a sharp instrument.

While the embodiments described above show the adapter 126 as having locking elements 166 protruding therefrom and pockets 168 formed on the instrument handle 104, in other embodiments, these features can be reversed. For example, the instrument handle 104 can include protruding locking elements 166 and the adapter 126 can include pockets. In some embodiments, each of the instrument handle 104 and the adapter 126 include both locking elements 166 and pockets 168.

Figure 18A:
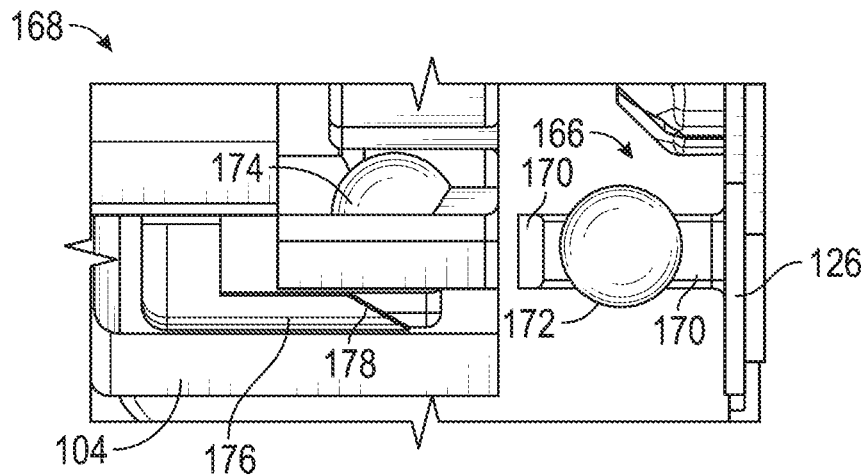
FIGS. 18A-18C provide views of an embodiment of an attachment mechanism during various stages of an attachment process.
Figure 18B:
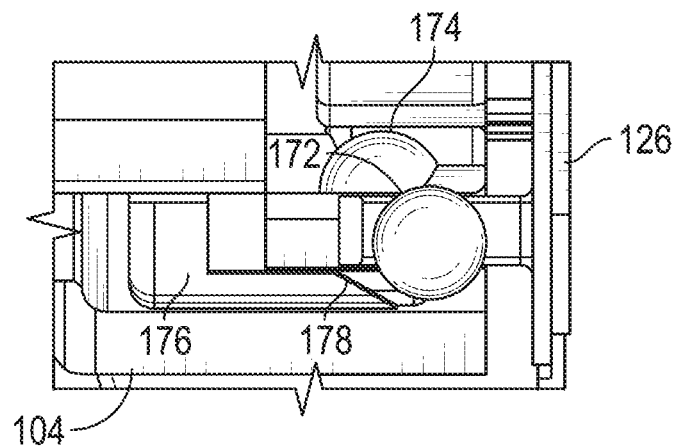
Figure 18C:
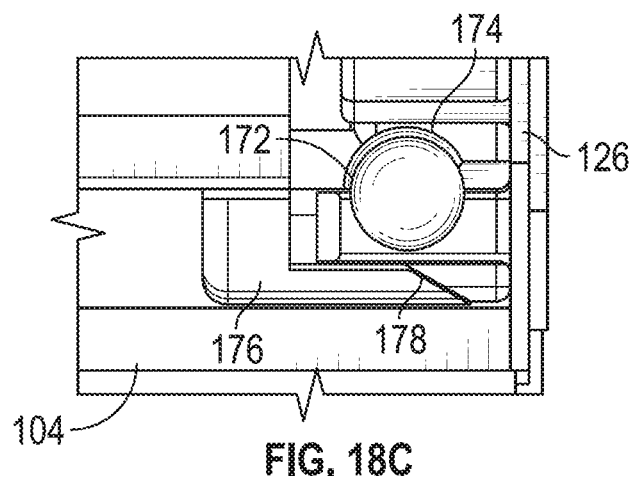

FIGS. 18A-18C provide additional detailed views of the locking elements 166 and pockets 168 of the attachment mechanism 160 illustrated in FIGS. 17A-17D. In this embodiment, the locking elements 166 include ball bearings 172 which are retained within a flange 170 that extends from the adapter 126. FIGS. 19A-19C described below illustrate how an embodiment with a ball bearings 172 which are retained within a flange 170 can be manufactured.

As illustrated in FIGS. 18A-18C, the pocket 168 can include a retaining surface 174. The retaining surface 174 can be configured to move or translate in a radial direction (up and down in the orientation illustrated in FIGS. 18A-18C. The retaining surface 174 can have a profile configured to correspond to the shape of the ball bearing 172. The retaining surface 174 can be biased in a radially outward (e.g., downward with reference to the orientation of the figures) direction. Biasing can be accomplished, for example, by use of a spring (not illustrated).

The pocket 168 can also include a collar 176. The collar 176 can include a ramped or sloped surface 178 as illustrated. The collar 176 can be moveable in the proximal and distal direction (e.g., right and left relative to the orientation of the figures). The collar 176 can be biased in the distal direction (e.g., toward the right in the figure), for example, by a spring (not illustrated). Interaction of the ball bearing 172, retaining surface 174, and collar 176 can allow for connection and disconnection of the locking element 166 to and from the pocket 168.

Example attachment will be described with reference to FIGS. 18A-18C. FIG. 18A illustrates the locking element 166 and the pocket 168 of the attachment mechanism 160 in an unattached configuration. FIG. 18B illustrates the locking element 166 and the pocket 168 in an intermediary position between the unattached configuration and an attached configuration. And, FIG. 18C illustrates the locking element 166 and the pocket 168 in the attached configuration. As illustrated, when the instrument handle 104 is inserted onto the adapter 126, the spring loaded internal collar 176 is pushed proximally inside of the case or housing of the instrument handle 104 (FIG. 19B). When the ball bearing 172 of the locking element 166 is aligned with a cup feature on the retaining surface 174, the ball bearing 172 moves into the cup and the collar 176 slides back down (FIG. 19C). In this position (FIG. 18C), the locking element 166 is secured within the pocket 168.

To detach, the collar 176 and the instrument handle 104 can be pulled proximally concurrently. When the collar 176 is retracted far enough for the slope or ramp surface 178 of the collar 176 to allow the ball bearing 172 to escape from the cup feature of the retaining surface 174, the locking element 166 disengages with the pocket 168 allowing the instrument 100 to be smoothly disconnected.

FIGS. 19A-19C provide multiple views of an example assembly of the locking element 166, although other embodiments are possible. The example assembly of FIGS. 19A-19C comprises a locking element 166, that includes a ball bearing 172 and a flange 170, on an adapter 126. In this embodiment, the ball bearing 172 is captured within the flange 170 between components of two layers or stacked plates of the adapter 126. FIG. 19A is a partially exploded perspective view of the adapter 126. FIG. 19B is a perspective view of the adapter 126 illustrating the locking element 166 in an assembled configuration. FIG. 19C is a cross-sectional view of the adapter 126 illustrating the locking element 166 in the assembled configuration.

As shown in FIG. 19A, the adapter 126 can comprise a stacked plate construction comprising a proximal plate 191 and a distal plate 1292 The flange 170 can extend from the proximal plate 191. The flange 170 includes a bore or hole extending there through for receiving the ball bearing 172. In the illustrated embodiment, the ball bearing 172 can be inserted into the flange 170 from the outer radial side of the flange 170. A protrusion 195 prevents the ball bearing 172 from being pushed all the way through the flange. As shown in the cross-sectional view of FIG. 19C, the protrusion 195 narrows the diameter of the hole through the flange 170 such that the ball bearing 172 cannot pass through the radial inner side of the flange.

The distal plate 192 can include a backstop 193, formed as a projection extending from the distal plate 192. When assembled, as shown in FIG. 19B, the backstop 193 extends through a corresponding opening 194 (as shown in FIG. 19A) in the proximal plate 191. In this position, the backstop 193 can retain the ball bearing 172 within the flange 170.

FIG. 20 illustrates another embodiment of an attachment mechanism 160. In this embodiment, the instrument handle 104 includes pinch levers 180. The pinch levers 180 can be attached to the instrument handle 104 by hinges 182 about which the pinch levers can pivot. A spring element 185 can be positioned to bias the pinch levers to a radially outward position in which a hooked end 184 of the pinch lever 180 engages a cantilever hook 186 that extends from the adapter 126.

To engage the attachment mechanism 160, the instrument handle is moved towards the adapter 126. The outer surface of the cantilever hooks 186 deflects the pinch levers 180 inward allowing the hooked ends 184 to pass and engage the cantilever hooks 186. To disengage, the pinch levers 180 can be pressed inwardly to such that the hooked ends 184 move free of the cantilever hooks 186.

FIG. 21 illustrates another embodiment of an attachment mechanism 160 that includes a stamped metal element 188 that is securely attached to the adapter 126. The instrument handle 104 includes a cantilever hook 187 that engages with an opening in the stamped metal element 188. The stamped metal element can be configured to be levered in and out by cantilever hook to allow for attachment.

Figure 22:
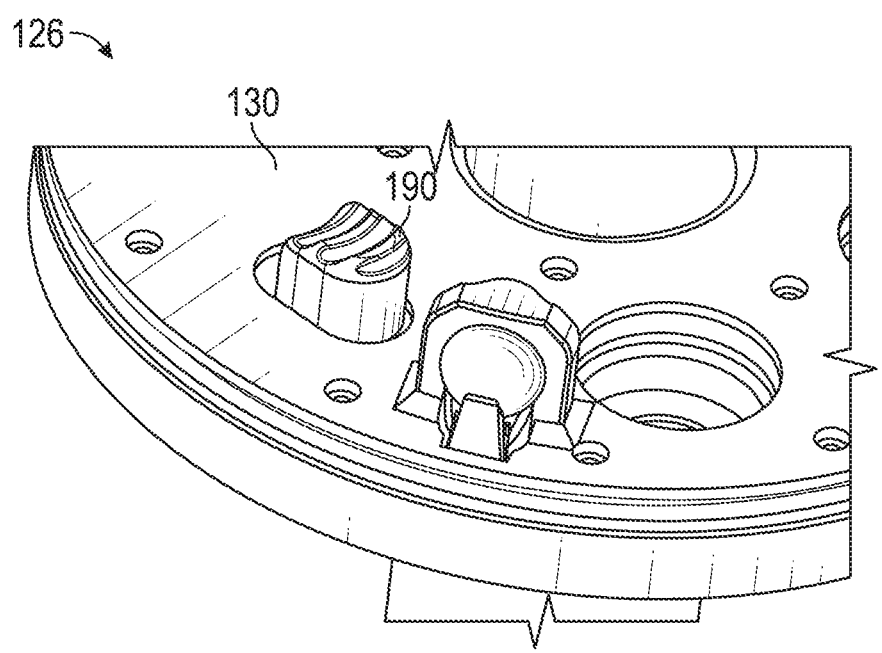
FIG. 22 is a perspective view of a proximal face of an embodiment of an adapter and illustrates that an adapter release mechanism can be positioned on the proximal face.

FIG. 22 is a perspective view of the proximal face 130 of an embodiment of the adapter 126 and illustrates that, in some embodiments, an adapter release mechanism 190 can be positioned on the proximal face 130. The adapter release mechanism 190 can be configured to be actuable to release the adapter 126 from the instrument drive mechanism 124. The adapter release mechanism 190 can be, for example, a button or slide toggle. Inclusion of the adapter release mechanism 190 on the proximal face 130 may prevent accidental removal of the adapter 126 because the adapter release mechanism 190 is inaccessible when the 100 is attached to the adapter 126. In other embodiments, the adapter release mechanism 190 may be included on other portions of the adapter 126, including portions that are accessible when the instrument 100 is attached to the adapter.

3. Implementing Systems and Terminology

Implementations disclosed herein provide systems, methods and apparatus for robotically-enabled medical systems. Various implementations described herein include robotically-enabled medical systems with high force instruments.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The position estimation and robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the term "approximately" or "about" refers to a range of measurements of a length, thickness, a quantity, time period, or other measurable value. Such range of measurements encompasses variations of +/−10% or less, preferably +/−5% or less, more preferably +/−1% or less, and still more preferably +/−0.1% or less, of and from the specified value, in so far as such variations are appropriate in order to function in the disclosed devices, systems, and techniques.

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A medical system, comprising:
   a medical instrument comprising an instrument handle and an elongated body, wherein the instrument handle is configured to attach to an adapter on an instrument drive mechanism such that a plurality of drive inputs on the instrument handle engage with a corresponding plurality of instrument drive outputs of the adapter; and
   an alignment mechanism comprising an alignment surface on the elongated body configured to rotate the instrument handle during attachment of the instrument handle to the adapter to provide rotational alignment between the medical instrument and the adapter such that the plurality of drive inputs are aligned with the plurality of drive outputs.

2. The system of claim 1, wherein the alignment mechanism extends along a longitudinal axis of the instrument handle.

3. The system of claim 1, wherein the alignment surface comprises a spiral surface on the elongated body.

4. The system of claim 1, wherein, when the instrument handle is attached to the adapter, a distal surface on the instrument handle opposes a proximal surface on the adapter.

5. The system of claim 1, wherein the instrument drive mechanism is positioned on a robotic arm.

6. The system of claim 5, wherein the robotic arm extends from a bed or a cart.

7. The system of claim 1, wherein the rotational alignment results in at least one locking element being aligned with and inserted into a corresponding pocket.

8. The system of claim 7, wherein the locking element is positioned on the adapter and the pocket is positioned on the handle.

9. The system of claim 7, wherein the locking element comprises a ball bearing.

10. The system of claim 1, wherein the rotational alignment is passive.

11. A medical system, comprising:
    a medical instrument configured for use during a robotically-enabled medical procedure, the medical instrument comprising:
       an elongated body extending between a distal end and a proximal end, the distal end configured to be inserted into a patient during a robotically-enabled medical procedure, and
       an instrument handle including a proximal face and a distal face, wherein the elongated body extends through the proximal face and the distal face, wherein the instrument handle comprises a plurality of drive inputs, wherein the distal face is configured to attach to an adapter on an instrument drive mechanism, and wherein the instrument drive mechanism comprises a plurality of drive outputs configured to engage with the plurality of drive inputs; and
    an alignment mechanism configured to rotate the instrument handle during attachment of the instrument handle to the adapter to provide rotational alignment between the medical instrument and the adapter, the alignment mechanism comprising:
       a first alignment structure on the medical instrument, wherein the first alignment structure comprises an alignment surface on the elongated body, and
       a second alignment structure on the adapter,
       wherein, as the medical instrument is attached to the adapter, the first alignment structure engages the second alignment structure to provide the rotational alignment such that the plurality of drive inputs on the instrument handle engage with the plurality of instrument drive outputs of the adapter.

12. The system of claim 11, wherein, when the instrument handle is attached to the adapter, the alignment mechanism extends along a longitudinal axis of the instrument handle.

13. The system of claim 11, wherein the first alignment surface comprises a spiral surface on the elongated body, and the second attachment structure comprises a bearing surface within an opening of adapter.

14. The system of claim 13, wherein the bearing surface comprises a ball bearing.

15. The system of claim 11, wherein the instrument drive mechanism is positioned on a robotic arm.

16. The system of claim 15, wherein the robotic arm extends from a bed or a cart.

17. The system of claim 11, wherein the rotational alignment results in at least one locking element being aligned with and inserted into a corresponding pocket.

18. The system of claim 17, wherein the locking element is positioned on the adapter and the pocket is positioned on the handle.

19. The system of claim 17, wherein the locking element is positioned on the handle and the pocket is positioned on the adapter.

* * * * *